US008454517B2

(12) United States Patent
Sato

(10) Patent No.: US 8,454,517 B2
(45) Date of Patent: Jun. 4, 2013

(54) ULTRASONIC DIAGNOSTIC APPARATUS AND ULTRASONIC DIAGNOSTIC METHOD

(75) Inventor: Takeshi Sato, Nasushiobara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 1264 days.

(21) Appl. No.: 11/121,078

(22) Filed: May 4, 2005

(65) Prior Publication Data
US 2005/0256404 A1 Nov. 17, 2005

(30) Foreign Application Priority Data

May 11, 2004 (JP) ................. P2004-141162

(51) Int. Cl.
A61B 8/14 (2006.01)
(52) U.S. Cl.
USPC ........................................................ 600/458
(58) Field of Classification Search
USPC .................. 600/437, 441, 443, 447, 453, 458
See application file for complete search history.

(56) References Cited

U.S. PATENT DOCUMENTS

| 5,577,505 | A | 11/1996 | Brock-Fisher et al. | |
|---|---|---|---|---|
| 5,632,277 | A | 5/1997 | Chapman et al. | |
| 5,678,553 | A | 10/1997 | Uhlendorf et al. | |
| 5,718,229 | A * | 2/1998 | Pesque et al. | 600/441 |
| 5,735,281 | A * | 4/1998 | Rafter et al. | 600/458 |
| 5,931,784 | A * | 8/1999 | Kajiwara et al. | 600/441 |
| 5,957,852 | A | 9/1999 | Hossack et al. | |
| 6,048,316 | A * | 4/2000 | Zhao et al. | 600/447 |
| 6,063,033 | A * | 5/2000 | Haider et al. | 600/447 |
| 6,095,980 | A * | 8/2000 | Burns et al. | 600/453 |
| 6,171,246 | B1 * | 1/2001 | Averkiou et al. | 600/458 |
| 6,210,334 | B1 * | 4/2001 | Phillips | 600/453 |
| 6,213,947 | B1 * | 4/2001 | Phillips | 600/443 |
| 6,319,203 | B1 | 11/2001 | Averkiou | |
| 6,458,084 | B2 * | 10/2002 | Tsao et al. | 600/443 |
| 6,494,841 | B1 * | 12/2002 | Thomas et al. | 600/447 |
| 6,497,665 | B1 * | 12/2002 | Hunt et al. | 600/458 |
| 6,508,766 | B2 * | 1/2003 | Sato et al. | 600/441 |
| 6,814,703 | B2 | 11/2004 | Sato | |
| 2003/0018259 | A1 * | 1/2003 | Kawagishi et al. | 600/443 |
| 2003/0073903 | A1 * | 4/2003 | Sato | 600/437 |

FOREIGN PATENT DOCUMENTS

| JP | 2002-11004 | 1/2002 |
|---|---|---|
| JP | 2002-537048 | 11/2002 |
| JP | 2003-500150 | 1/2003 |
| JP | 2003-102726 | 4/2003 |
| JP | 2004-24876 | 1/2004 |

* cited by examiner

Primary Examiner — Long V. Le
Assistant Examiner — Bo J Peng
(74) Attorney, Agent, or Firm — Oblon, Spivak, McClelland, Maier & Neustadt, L.L.P.

(57) ABSTRACT

An ultrasonic diagnostic apparatus 10 comprises an ultrasonic transmitter unit 13,15, an ultrasonic receiving unit 13,17, an extracting unit 17, a filter unit and an adder unit 19c,21c. The ultrasonic transmitter unit 13,15 transmits ultrasonic varied at least one of phase and amplitude to an object. The ultrasonic receiving unit 13,17 receives ultrasonic echoes. The extracting unit 17 extracts a first nonlinear signal obtained through modulating the amplitude and a second linear signal obtained through modulating the phase from common ultrasonic echoes. The filter unit processes a filter process to the first nonlinear signal and the second nonlinear signal with at least two deferent sets of a middle frequency and a width of a band. The adder unit 19c,21c performs weighted addition to signals obtained through the first nonlinear signal and the second nonlinear signal according to a depth of the object.

6 Claims, 11 Drawing Sheets

ULTRASONIC DIAGNOSTIC APPARATUS AND ULTRASONIC DIAGNOSTIC METHOD

CROSS REFERENCES TO RELATED APPLICATIONS

The present application relates to and incorporates by reference Japanese Patent application No. 2004-141162 filed on May 11, 2004.

BACKGROUND OF THE INVENTION

1. Field of the Invention

The present invention relates to an ultrasonic diagnostic apparatus and an ultrasonic diagnostic method using nonlinear signals from a living body or ultrasonic contrast medium.

2. Description of the Related Art

An ultrasonic apparatus can noninvasively obtain a tomographic image of soft tissues inside a living body from the surface of the body using reflection of an ultrasonic wave and has advantages such as compactness, low price, capability of real time imaging, increased safety due to a lack of X-ray dosing, capability of blood flow imaging, etc., when compared to other diagnostic devices, such as X-ray diagnostic apparatus, X-ray CT apparatus, MRI apparatus or nuclear medicine diagnostic apparatus, and the like. Because of such advantages, ultrasound is currently widely used in many medical fields such as cardiac medicine, abdominal medicines such as gastroenterology, urology, obstetrics, gynecology, as well as others.

There are a variety of imaging methods for the ultrasonic diagnostic apparatus. "Contrast Echo" method is one of the important techniques to obtain an ultrasonic image in which scattered echo signals are enhanced by using an ultrasonic contrast medium containing microbubbles injected into a blood vessel of an object.

Recently, new contrast media for intravenous injection have emerged and imaging methods suitable for these contrast media have also been developed. For example, such methods include a Filter method (an imaging method using one pulse per scanning line: U.S. Pat. No. 5,678,553), a Doppler method (an imaging method using more than two in-phase pulses per scanning line), a Phase Inversion method (an imaging method using two 1800 out-of-phase pulses per scanning line: U.S. Pat. No. 5,632,277), a Phase Inversion Doppler method (an imaging method using more than three pulses alternated by 180° from pulse to pulse per scanning line: U.S. Pat. No. 6,095,980), the contents of which are herein incorporated by reference.

When performing a Contrast Echo method with any of the above methods, conventionally ultrasonic waves with medium or high acoustic pressure, such as MI (mechanical index: a value obtained by normalizing peak of negative sound pressure by a reference sound pressure of 1 Mpa) value of more than 0.5 have been used. This is typically done to obtain a prominent contrast enhancement effect by collapsing the microbubbles in the contrast medium. For example, when using one of widely used contrast medium, Levovist, manufactured by Schering, the image may not be properly enhanced unless ultrasonic waves with high acoustic pressure, such as those having an MI value of more than 0.8 are used.

Transmission of ultrasonic waves with high acoustic pressure and the subsequent collapse of microbubbles greatly affects ultrasonic imaging. When an ultrasonic wave with high acoustic pressure is propagated through tissue, a harmonic component is generated in an echo. However, the above-mentioned Filter method or Phase Inversion method can not separate a harmonic component from tissues (hereinafter "THI component") from a harmonic component from bubbles. Accordingly an image of bubbles obtained with the Filter method or the Phase Inversion method may not have enough contrast, and it may be difficult to distinguish between blood flow and a parenchymal contrast-enhancement in a contrast echo image.

Further, a collapse of bubbles creates a broadband Doppler signal when more than two ultrasonic beams are transmitted per scanning line. This broadband Doppler signal, called a pseudo-Doppler signal, can be utilized to produce an image because tissue and THI components in the fundamental signal can be suppressed by processing high-pass filter to suppress a signal whose motion is slow.

However, a color Doppler image based on the pseudo-Doppler signals would result in an image of thin blood vessels and contrast-enhancement in parenchyma with many aliasing points, which does not indicate proper blood flow velocities. Because the pseudo-Doppler signals unlike normal Doppler signals from blood flow do not indicate proper blood flow directions. Therefore, in most cases when an ultrasonic image obtained with contrast echo method is displayed, power Doppler is used instead of color Doppler, which is generally suitable for showing blood flow velocity.

Accordingly, in order to solve these problems, a system capable of performing good color Doppler imaging using an ultrasonic contrast medium, which achieves enhancement even if a MI value is 0.1 or lower, is proposed (see, for example, Japanese Unexamined Patent Application Publication No. 2003-102726). According to the system, on condition that the MI is low and the occurrence of THI components is suppressed, harmonic signals reflected from the contrast medium are extracted and a power signal and a velocity signal from the contrast medium are calculated. On the basis of the power signal, the velocity signal, and B-mode information of fundamental wave, only a B-mode image is displayed in grayscale before the contrast medium is injected. When blood flow in vessels is enhanced by the contrast medium, the direction of blood flow is displayed in red or blue. When blood flow in parenchyma is enhanced by the contrast medium, blood flow is displayed in green.

The system uses a very low ultrasonic power at which the MI value is 0.1 or lower. In addition, since second higher harmonic wave is used, imaging is seriously affected by attenuation dependent on frequency. Disadvantageously, therefore, the S/N ratio may be insufficient, resulting in poor penetration.

In principle, signals obtained by phase inversion or phase inversion Doppler are even-order higher harmonic wave. Accordingly, as a nonlinear signal capable of being used on condition that bubbles are not disrupted in filtering, phase inversion, and phase inversion Doppler, second higher harmonic wave are used practically. Regarding available higher harmonic wave other than the second higher harmonic wave, principally, third higher harmonic wave are obtained by filtering. Disadvantageously, a probe for a very wide band of frequencies is required and imaging with the third higher harmonic wave is seriously affected by attenuation dependent on frequency. Therefore, the use of the third higher harmonic wave is not adequate for the purpose of increasing penetration.

Generally, according to techniques using second higher harmonic wave, sensitivity is low. As solutions to harmonic problems, e.g., approaches using nonlinear signals of fundamental wave area are proposed. According to one of the approaches, a transmission pulse is transmitted two times such that the amplitude of the first pulse is different from that of the second and received signals are subjected to gain compensation, thus obtaining the different there between (see, for example, U.S. Pat. No. 5,577,505). According to another approach, a transmission pulse is transmitted two times such that the amplitude and the phase of the first pulse are different from those of the second (see, for example, U.S. Pat. No. 6,063,033). According to still another approach, second higher harmonic wave is obtained with high sensitivity by a pulse compression technique using a chirp signal (see, for example, U.S. Pat. No. 6,213,947).

In the above conventional solutions to the degradation in sensitivity caused by the use of second higher harmonic wave, i.e., the approach using nonlinear signals of fundamental wave area, the approach for changing both the amplitude and the phase of transmission pulse, and the approach for obtaining second higher harmonic wave with high sensitivity based on the pulse compression technique using a chirp signal, amplitude information such as B-mode information is merely used for imaging. In contrast echo imaging, therefore, velocity information of blood flow cannot be extracted from nonlinear signals of fundamental wave area with accuracy.

Further, not only in contrast echo imaging, it is desired to obtain nonlinear signals from living body with high sensitivity and high penetration.

SUMMARY OF THE INVENTION

Accordingly, the present invention has been made in light of the conventional situations, and it is an object of the present invention to provide an ultrasonic diagnostic apparatus and an ultrasonic diagnostic method capable of obtaining nonlinear signals from living body with high sensitivity and high penetration.

Furthermore, it is another object of the present invention to provide an ultrasonic diagnostic apparatus and an ultrasonic diagnostic method capable of achieving high resolution and high penetration in contrast echo imaging in which ultrasonic waves are transmitted at low MI.

In an aspect, to achieve the object, the present invention provides an ultrasonic diagnostic apparatus comprising an ultrasonic transmitter unit for transmitting an ultrasonic wave varied in at least one of phase and amplitude to an object, an ultrasonic receiving unit for receiving ultrasonic echoes generated by transmitting the ultrasonic wave, an extracting unit for extracting a first nonlinear signal obtained through modulating the amplitude of the ultrasonic wave and a second nonlinear signal obtained through modulating the phase of the ultrasonic wave from common ultrasonic echoes on a same scanning line, a filter unit for processing either a filter process and a process equivalent to the filter process either to the first nonlinear signal and the second nonlinear signal and to the first nonlinear signal processed a designated process and the second nonlinear signal processed the designated process with at least two deferent sets of a middle frequency and a width of a band, and an adder unit for performing weighted addition to signals obtained through the first nonlinear signal and the second nonlinear signal subjected to either the filter process and the process equivalent to the filter process according to a depth of the object.

Furthermore, in an aspect, to achieve the object, the present invention provides an ultrasonic diagnostic apparatus comprising an ultrasonic transmitter unit for transmitting an ultrasonic wave varied in at least one of phase and amplitude to an object and an ultrasonic receiving unit for receiving ultrasonic echoes generated by transmitting the ultrasonic wave, wherein the ultrasonic transmitter unit is configured to transmit the ultrasonic wave according to a transmitting pulse sequence which makes it possible to obtain at least two of a first nonlinear signal obtained through modulating amplitude of the ultrasonic wave, a second nonlinear signal obtained through modulating phase of the ultrasonic wave and a third nonlinear signal obtained through modulating the amplitude and the phase from common ultrasonic echoes on a same scanning line.

Furthermore, in an aspect, to achieve the object, the present invention provides an ultrasonic diagnostic apparatus comprising an ultrasonic transmitter unit for transmitting an ultrasonic wave varied in phase and amplitude to an object, an ultrasonic receiving unit for receiving ultrasonic echoes generated by transmitting the ultrasonic wave, an extracting unit for extracting a nonlinear signal obtained from the ultrasonic echoes by modulating the phase and the amplitude of the ultrasonic wave, a filter unit for processing either a filter process and a process equivalent to the filter process either to the nonlinear signal and to the nonlinear signal processed a designated process with at least two different sets of a middle frequency and a width of a band, and an adder unit for performing weighted addition to signals obtained through the nonlinear signal subjected to either the filter process and the process equivalent to the filter process according to a depth of the object.

Furthermore, in an aspect, to achieve the object, the present invention provides an ultrasonic diagnostic method comprising transmitting an ultrasonic wave varied in at least one of phase and amplitude to an object, receiving ultrasonic echoes generated by transmitting the ultrasonic wave, extracting a first nonlinear signal obtained through modulating the amplitude of the ultrasonic wave and a second nonlinear signal obtained through modulating the phase of the ultrasonic wave from common ultrasonic echoes on a same scanning line, processing either a filter process and a process equivalent to the filter process either to the first nonlinear signal and the second nonlinear signal and to the first nonlinear signal processed a designated process and the second nonlinear signal processed the designated process with at least two different sets of a middle frequency and a width of a band, and performing weighted addition to signals obtained through the first nonlinear signal and the second nonlinear signal processed either the filter process and the process equivalent to the filter process according to a depth of the object.

Furthermore, in an aspect, to achieve the object, the present invention provides an ultrasonic diagnostic method comprising transmitting an ultrasonic wave varied in at least one of phase and amplitude to an object and receiving ultrasonic echoes generated by transmitting the ultrasonic wave, wherein the ultrasonic wave is transmitted according to a transmitting pulse sequence which makes it possible to obtain at least two of a first nonlinear signal obtained through modulating amplitude of the ultrasonic wave, a second nonlinear signal obtained through modulating phase of the ultrasonic wave and a third nonlinear signal obtained through modulating the amplitude and the phase from common ultrasonic echoes on a same scanning line.

Furthermore, in an aspect, to achieve the object, the present invention provides an ultrasonic diagnostic method comprising transmitting an ultrasonic wave varied in phase and amplitude to an object, receiving ultrasonic echoes generated by transmitting the ultrasonic wave, extracting a nonlinear signal obtained from the ultrasonic echoes by modulating the phase and the amplitude of the ultrasonic wave, processing either a filter process and a process equivalent to the filter process either to the nonlinear signal and to the nonlinear signal processed a designated process with at least two different sets of a middle frequency and a width of a band, and performing weighted addition to signals obtained through the nonlinear signal subjected to either the filter process and the process equivalent to the filter process according to a depth of the object.

In the ultrasonic diagnostic apparatus and the ultrasonic diagnostic method as described above, it is possible to obtain nonlinear signals from living body with high sensitivity and high penetration.

Furthermore, it is possible to achieve high resolution and high penetration in contrast echo imaging in which ultrasonic waves are transmitted at low MI.

DESCRIPTION OF THE PREFERRED EMBODIMENTS

Embodiments of an ultrasonic diagnostic apparatus and an ultrasonic diagnostic method according to the present invention will be described with reference to the accompanying drawings.

Figure 1:
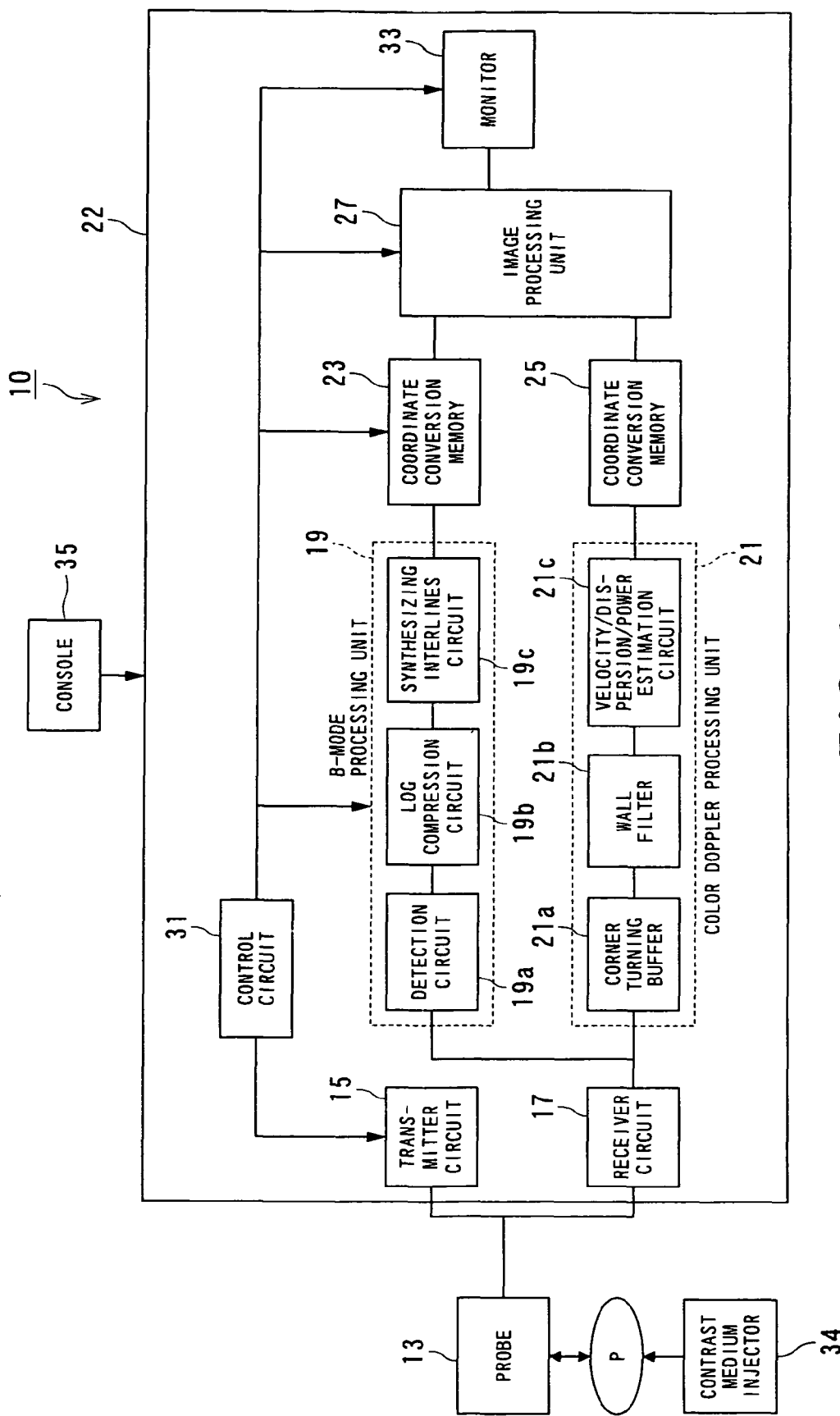
FIG. 1 is a block diagram of an ultrasonic diagnostic apparatus according to an embodiment of the present invention.
Figure 2:
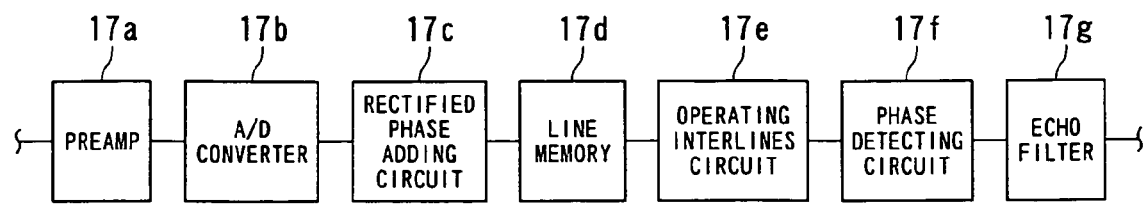
FIG. 2 is a block diagram of a receiver circuit 17 included in the ultrasonic diagnostic apparatus indicated in FIG. 1.
Figure 3:
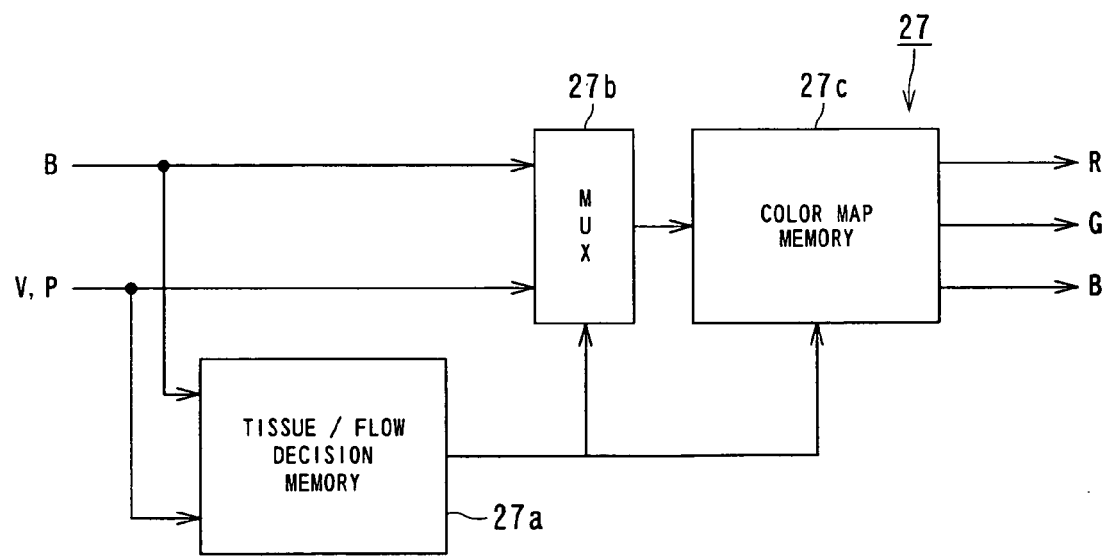
FIG. 3 is a block diagram of an image processing unit included in the ultrasonic diagnostic apparatus indicated in FIG. 1.

FIG. 1 is a block diagram of an ultrasonic diagnostic apparatus according to an embodiment of the present invention. FIG. 2 is a block diagram of a receiver circuit 17 included in the ultrasonic diagnostic apparatus 10 indicated in FIG. 1. FIG. 3 is a block diagram of an image processing unit 27 included in the ultrasonic diagnostic apparatus 10 indicated in FIG. 1.

The ultrasonic diagnostic apparatus 10 includes an ultrasonic probe 13, a transmitter circuit 15, a receiver circuit 17, a B-mode processing unit 19, a color Doppler processing unit 21, a coordinate conversion memory for B-mode processing 23, a coordinate conversion memory for color Doppler processing 25, an image processing circuit 27, a control circuit 31, a monitor 33, and a console 35.

The ultrasonic probe 13 includes piezoelectric transducers as elements transforming sound/electric reversibly like piezoelectric ceramics. The piezoelectric transducers, provided on the top of the probe 13 in an array, have the function to transmit ultrasonic waves according to voltage pulses impressed from the transmitter circuit 15 and to receive ultrasonic echoes and transform the ultrasonic echoes to electric signals.

The transmitter circuit 15, connected to the probe 13, includes a pulse generator, a transmission delay circuit and a pulser (not shown in FIG. 1). The pulse generator in the transmitter circuit 15 has the function to generate transmission pulses repeatedly with AM (Amplitude Modulation) (PM: Phase Modulation) or AM and PM at a pulse repetition frequency fr (Hz) (period: 1/fr (sec.)) of 5 kHz for example. These transmission pulses are distributed to each channel to be sent to the transmission delay circuit. The transmission delay circuit has the function to provide each of the transmission pulses with a delay time necessary for concentrating ultrasonic waves to form a beam and determining the transmission directivity. The transmission delay circuit is triggered by timing signals from a trigger signal generator (not shown). The pulsar provides the probe 13 with a voltage pulse each channel when it receives the transmission pulse from the transmission delay circuit. Consequently, it is possible to transmit the ultrasonic beams to the object P.

Referring to FIG. 2, the receiver circuit 17 includes a preamplifier (preamp) 17a, an analog-to-digital (A/D) converter 17b, a rectified phase adding circuit 17c, a line memory 17d, an operating interlines circuit 17e, a phase detecting circuit 17f, and an echo filter 17g. In the receiver circuit 17, the components are connected in series. The receiver circuit 17 receives ultrasonic echoes from an ultrasonic probe 13, generates base band signals, and supplies the signals to each of a B-mode processing unit 19 and a color Doppler processing unit 21. The units 19 and 21 are arranged downstream of the receiver circuit 17. The ultrasonic probe 13 and a transmitter circuit 15 function as ultrasonic transmitter unit of the ultrasonic diagnostic apparatus 10. The ultrasonic probe 13 and the receiver circuit 17 function as ultrasonic receiving unit of the ultrasonic diagnostic apparatus 10.

The preamplifier 17a of the receiver circuit 17 has the function to amplify an echo signal received in the receiver circuit 17 through the probe 13 at each channel and to give the echo signal amplified to the A/D converter 17b.

The A/D converter 17b converts echo signals amplified by the preamp 17a into digital signals and then supplies the digital signals to the rectified phase adding circuit 17c.

The rectified phase adding circuit 17c performs a rectifying and adding process to the digital signals serving as the echo signals supplied from the A/D converter 17b to produce an RF signal. In other words, in the rectified phase adding circuit 17c, delay time required to determine the receiving directivity is assigned to each echo signal and the resultant signals are added. By this addition, an RF signal having enhanced components reflected in the direction corresponding to the receiving directivity of the echo signals is produced. On the basis of the receiving directivity and transmitting directivity, the synthetic directivity of ultrasonic transmission and reception, i.e., a "scan line" is determined.

The line memory 17d temporarily stores RF signals, which are produced in a plurality of ultrasonic transmissions and receptions by the rectified phase adding circuit 17c.

The operating interlines circuit 17e reads a plurality of RF signals, obtained from the same scan line, from the line memory 17d and multiplies the signals by predetermined coefficients for receiving filter to produce a nonlinear signal. In other words, ultrasonic waves transmitted to a object P are subjected to amplitude modulation (AM), phase modulation (PM), or both AM and PM. When the RF signals are subjected to gain compensation, a nonlinear signal based on AM, that based on PM, or that based on both AM and PM can be produced from common ultrasonic echoes from the same scan line.

A function of transmitting and receiving ultrasonic waves according to a predetermined transmission pulse sequence and a function of producing a nonlinear signal by the operating interlines circuit 17e provide extracting unit for extracting a plurality of nonlinear signals from common ultrasonic echoes in the ultrasonic diagnostic apparatus 10. Methods (signal extracting methods) for extracting a nonlinear signal include a method for extracting a nonlinear signal based on AM, a method for extracting a nonlinear signal based on PM, and a method for extracting a nonlinear signal based on both AM and PM. Setting a transmission pulse sequence and the process of the operating interlines circuit 17e achieve the extraction of nonlinear signals from common ultrasonic echoes according to at least two different signal extracting methods.

The phase detecting circuit 17f receives a nonlinear signal based on AM or PM from the operating interlines circuit 17e. For the nonlinear signal based on AM, the circuit 17f mixes components of the nonlinear signal at approximately the center frequency of transmitted ultrasonic waves, thus producing a base band signal (I and Q signals). For the nonlinear signal based on PM, the circuit 17f mixes components of the nonlinear signal at a frequency that is approximately twice as high as the center frequency of transmitted ultrasonic waves, thus producing a base band signal (I and Q signals). In this instance, the frequency for mixing is changed depending on the depth of a target part in the object P, i.e., the distance from the plane for ultrasonic transmission and reception of the ultrasonic probe 13 to a target point.

The echo filter 17g serves as a band pass filter and has a function of executing a filtering process to the base band signals, produced by the phase detecting circuit 17f, using filter coefficients. The filter coefficients are set so as to correspond to the base band signal based on AM and that based on PM, respectively. Thus, in the ultrasonic diagnostic apparatus 10, the echo filter 17g serves as filter unit for performing the filtering process to the base band signals as nonlinear signals. The base band signals subjected to the filtering process are supplied to the B-mode processing unit 19 or the color Doppler processing unit 21.

Instead of the filtering process to the base band signals, prior to phase detection, RF signals can be subjected to a process equivalent to the filtering process.

On the other hand the B-mode processing unit 19 includes detection circuit 19a, a log compression circuit 19b and a synthesizing interlines circuit 19c as shown in FIG. 1. The detection circuit 19a has the function to detect an envelope of a base band signal output from the receiver circuit 17 and to obtains a B-mode signal in respective scanning lines constituting a B-mode image. The log compression circuit 19b has the function to perform logarithmic compression on the B-mode signal.

A synthesizing interlines circuit 19c has a function of assigning weights to two B-mode signal values based on AM and PM, respectively, according to the depth of a target part in the object P and adding the resultant signal values. In this instance, in a shallow part of the object P, the weight for the B-mode signal value based on PM is increased. In a deep part of the object P, the weight for the B-mode signal value based on AM is increased. In other words, in the B-mode processing unit 19 of the ultrasonic diagnostic apparatus 10, the synthesizing interlines circuit 19c serves as adder unit for performing weighted addition to the nonlinear signals according to the depth of a target part in the object P.

The color Doppler processing unit 21 includes a CTB (Corner Turning Buffer) 21a, a wall filter 21b and a velocity/dispersion/power estimation circuit 21c.

A corner turning buffer (CTB) 21a temporarily stores a time-series data sequence of the base band signals supplied from the receiver circuit 17. The data sequence of the base band signals stored in the CTB 21a is output to a wall filter 21b in a predetermined order.

The wall filter 21b separates noise components unnecessary for color imaging of a blood flow image from the base band signal including fundamental components and that including harmonic components.

A velocity/dispersion/power estimation circuit 21c operates the correlation between echo signals, which have different phases each other to calculate an average frequency. The velocity/dispersion/power estimation circuit 21c calculates blood flow velocity, dispersion, and power estimation in color Doppler imaging. On the basis of the extracted base band signals as the fundamental components and the harmonic components, the velocity/dispersion/power estimation circuit 21c estimates a power signal constituting a power image for each scan line and a velocity signal constituting a velocity image for each scan line.

The velocity/dispersion/power estimation circuit 21c estimates a power signal value and a velocity signal value every nonlinear signal obtained by each signal extracting method, weights the estimated power signal values and the velocity signal values according to the depth of a target part in the object P, and adds the paired weighted values, respectively. Thus, in the color Doppler processing unit 21 of the ultrasonic diagnostic apparatus 10, the velocity/dispersion/power estimation circuit 21c serves as adder unit for performing weighted addition to the nonlinear signals according to the depth of a target part in the object P.

A coordinate conversion memory 23 for the B-mode processing unit converts a signal sequence for each scan line, i.e., the B-mode signal supplied from the B-mode processing unit 19 into data of an orthogonal coordinate system based on spatial information of an ultrasound scan. A coordinate conversion memory 25 for the color Doppler processing unit converts a signal sequence for each scan line, i.e., the power signal and the velocity signal supplied from the color Doppler processing unit 21 into data of the orthogonal coordinate system based on spatial information of an ultrasound scan.

The image processing circuit 27 has the function to determine a signal value as a pixel value to be displayed in an image among a B-mode signal value B, a power signal value P and a velocity signal value V for each pixel input from the coordinate conversion memories 23,25 and to assign one of the possible predetermined color and brightness according to the determined signal value. So, by the image processing circuit 27, the ultrasonic diagnostic apparatus 10 includes the function as an image processing unit for synthesizing one or both of a power image obtained through the power signal values and a velocity image obtained through the velocity signal values to a B-mode image obtained through the B-mode signal values.

The image processing circuit 27 includes a TFD (Tissue/Flow Decision) memory 27a, a multiplexer 27b, and a color map memory 27c as shown in FIG. 3.

The TFD memory 27a has the function to input a B-mode signal value, a power signal value P and a velocity signal value V for each pixel and to decide which value (B, P or V) is to be used as a pixel value in an image according to a predetermined function table and the function to output the decided signal value information for each pixel to be used in the image to the multiplexer 27b.

The multiplexer 27b has the function as a switch for selectively outputting one of the B, P, and V signal values for each pixel to the next device according to the signal value information decided on the TFD memory 27a.

The color map memory 27c has the function as a memory witch stores a color map assigned in the respective signal values and the function to produce a compound image consisting of the B-mode, power and velocity signals by assigning a certain color and brightness according to the signal value of each pixel input from the multiplexer 27b and to output the image to the monitor 33.

On the other hand, in FIG. 1, the control circuit 31 has the function to control processes of the ultrasonic diagnostic apparatus 10 as a central control unit for the whole system.

The monitor 33, such as a CRT, etc., has the function to display a tomographic image of the internal tissues of the object according to the input video signal. The monitor 33 may also display a compound image including B-mode, power and velocity signals produced by the image processing circuit 27.

The console 35, connected to the main unit 22 of the apparatus, includes input devices (mouse, trackball, mode-change switches, keyboard, etc.) for an operator to input variety of directions, orders, information into the main unit 22 and to set an ROI, as well as other functions.

A contrast medium injector 34 is arranged in the vicinity of the object P. A contrast medium is injected into the object P from the contrast medium injector 34, so that ultrasonic imaging using the contrast medium can be performed.

Next, Procedures of acquiring, processing, and displaying an ultrasonic image according to the ultrasonic diagnostic apparatus 10 will be discussed. These procedures make it possible to display an ultrasonic blood flow image indicating proper blood flow directions using a contrast medium and to clearly distinguish blood flow, contrast-enhancement in parenchyma and non-contrasted tissues on the image.

Figure 4:
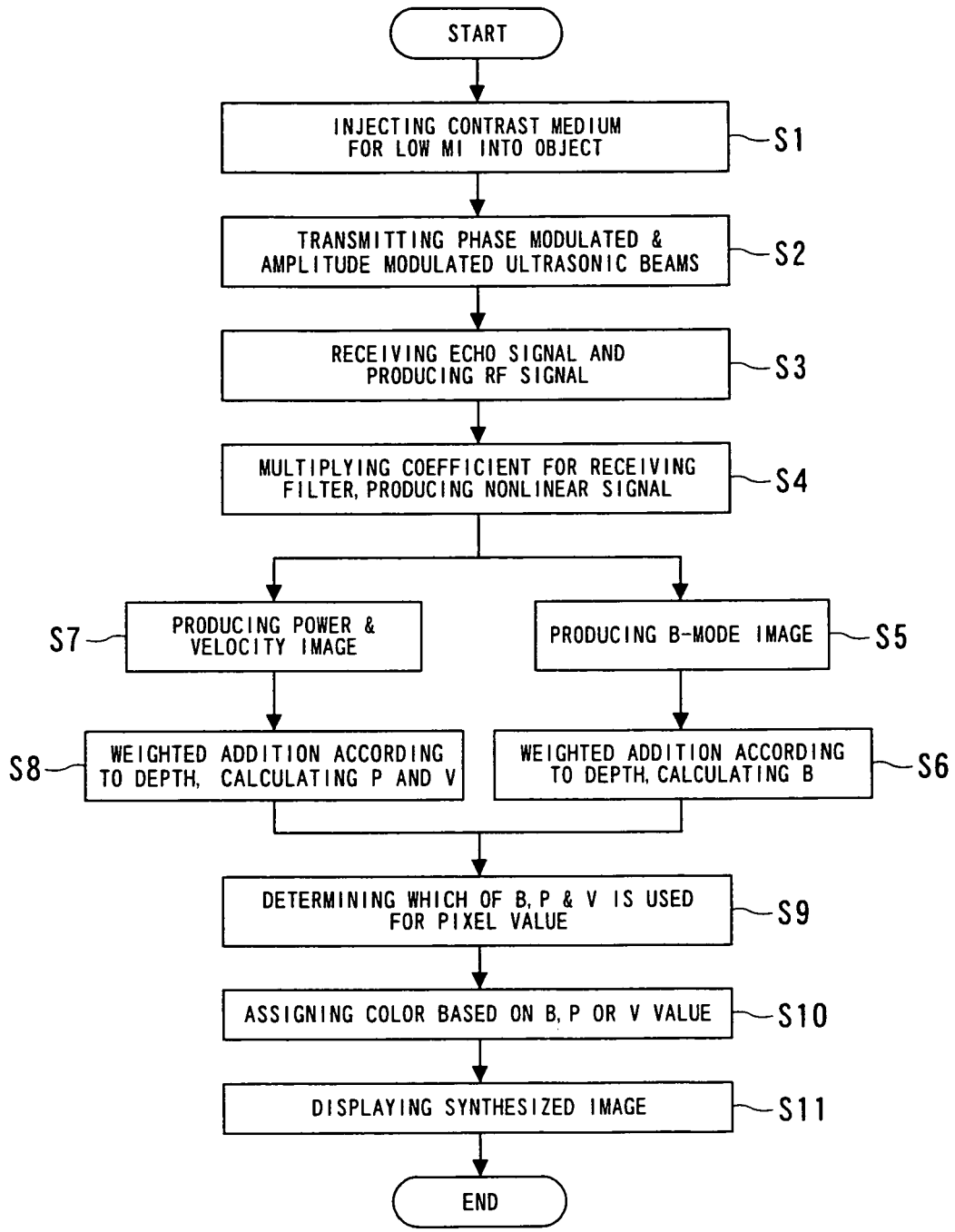
FIG. 4 is a flowchart explaining a process including ultrasonic image acquisition, synthesis, and display, the process being realized by the ultrasonic diagnostic apparatus shown in FIG. 1.

FIG. 4 is a flowchart explaining a process including ultrasonic image acquisition, synthesis, and display, the process being realized by the ultrasonic diagnostic apparatus 10 shown in FIG. 1. In FIG. 4 the symbols attached numbers indicate each step of the flowchart.

In step S1, an ultrasonic contrast medium is injected into the object P. The following ultrasonic contrast medium is desired: At a low sound pressure, e.g., when the mechanical index (MI) of ultrasonic waves transmitted to the object P is about 0.1, a nonlinear signal included in reflected waves (reflected echoes) can be obtained at a relatively high intensity. In other words, a contrast medium whereby a nonlinear signal enough to diagnose the object P can be received is used. For example, SonoVue, the Bracco's contrast medium, can be used.

When such a contrast medium is used at such a low sound pressure that the MI is about 0.1, the present inventor has found the following advantages: First, since the disruption of bubbles is less, the occurrence of pseudo Doppler signals incorrectly indicating the direction of blood flow can be reduced as compared to the transmission of ultrasonic waves at high MI. When ultrasonic waves are transmitted to one scan line twice or more, the disruption of bubbles causes the generation of pseudo Doppler signals.

Second, at such a low sound pressure that the MI is about 0.1, the harmonic components (THI components) from tissue can be minimized. The THI components are caused by nonlinearity based on the distortion of ultrasonic waveform in propagation. At low sound pressure, the distortion of ultrasonic waveform in propagation is little.

In step S2, the object P is irradiated with ultrasonic waves a plurality of times according to such a predetermined transmission pulse sequence that amplitude modulation (AM) and phase modulation (PM) can simultaneously be performed. In other words, the transmitter circuit 15 generates a pulse signal to the ultrasonic probe 13 with respect to the same scan line at predetermined time intervals (PRF: pulse repetition frequency). The ultrasonic probe 13 transmits an ultrasonic pulse, e.g., three times to the object P.

Assuming that the ratio between transmission voltages (amplitudes) of the ultrasonic pulses is expressed as a0:a1:a2 and a pulse sequence is expressed in a sequence of numbers in transmitting order using positive and negative signs which indicate a 180° phase shift between the pulses. For example, the transmitter circuit 15 transmits ultrasound three times at a center frequency f0 according to the transmission pulse sequence of [a0, a1, a2]=[−0.5, −1, 1].

In other words, ultrasonic pulses are transmitted to one scan line such that a voltage of which the ratio is 0.5 (e.g., a voltage at which MI=0.05) is used first time, a voltage of which the ratio is 1 (e.g., a voltage at which MI=0.1) is used second and third times, the first and second transmission pulses are in phase, and the third transmission pulse is 180° out of phase with the first and second transmission pulses.

Figure 5:
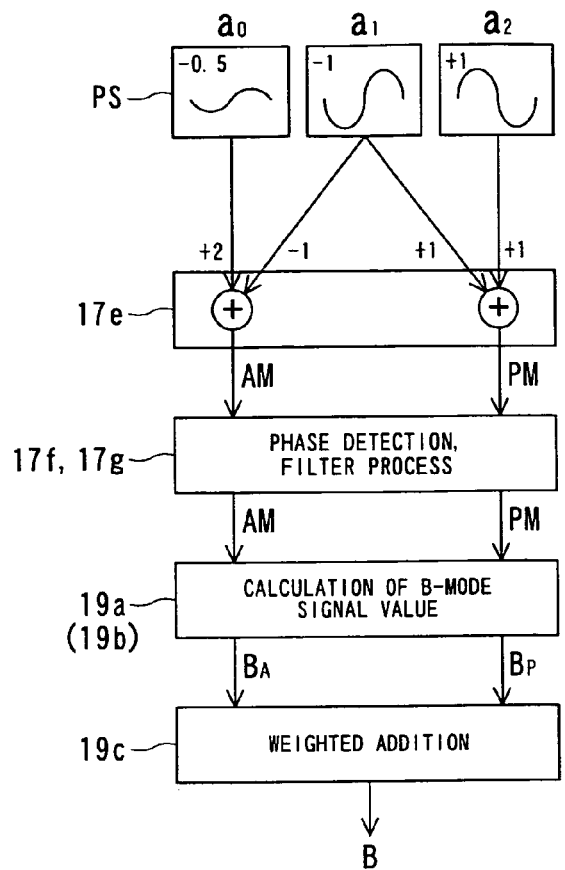
FIG. 5 is a diagram of a procedure of the ultrasonic diagnostic apparatus shown in FIG. 1 on the occasion that the ultrasonic diagnostic apparatus simultaneously performs amplitude modulation and phase modulation, transmits amplitude-modulated and phase-modulated ultrasonic waves, and receives reflected waves to produce a B-mode signal B through the B-mode processing unit.

FIG. 5 is a diagram of a procedure of the ultrasonic diagnostic apparatus 10 shown in FIG. 1 on the occasion that the ultrasonic diagnostic apparatus 10 simultaneously performs amplitude modulation and phase modulation, transmits amplitude-modulated and phase-modulated ultrasonic waves, and receives reflected waves to produce a B-mode signal B through the B-mode processing unit 19. FIG. 5 shows a transmission pulse sequence PS transmitted from the transmitter circuit 15 to the ultrasonic probe 13.

A series of pulses are generated at different drive voltages. The other conditions are the same. A transmission frequency is set such that the highest sensitivity is achieved in the frequency band of the probe in consideration of frequency-dependent attenuation in vivo. It is, therefore, necessary that the transmitter circuit 15 can transmit ultrasonic pulses at least two different voltages.

In addition to the above structure in which the amplitude of ultrasound transmitted is modulated by voltage control in ultrasound transmission, the following structure can be used: Voltage to be applied in ultrasound transmission is kept constant and the number of channels to be used in the ultrasonic probe 13 is controlled, thus controlling the amplitude of ultrasound transmitted. For example, when ultrasonic waves are transmitted by the ultrasonic probe 13 including a one-dimensional array of transducers according to a pulse sequence of [−0.5, −1, 1], the number of channels used in the transmission of [−0.5] is reduced to half that used in the transmission of [1].

In other words, instead of the three transmissions of [−0.5, −1, 1], ultrasound can be transmitted four times according to a pulse sequence of [a0, a1, a2, a3]=[−0.5 (even), −0.5 (odd), −1 (all), 1 (all)]. The "even" means that only even-numbered transducers (channels) in a transmission aperture are driven. The "odd" means that only odd-numbered transducers in the transmission aperture are driven. The "all" means that all of the transducers in the transmission aperture are driven.

Figure 6:
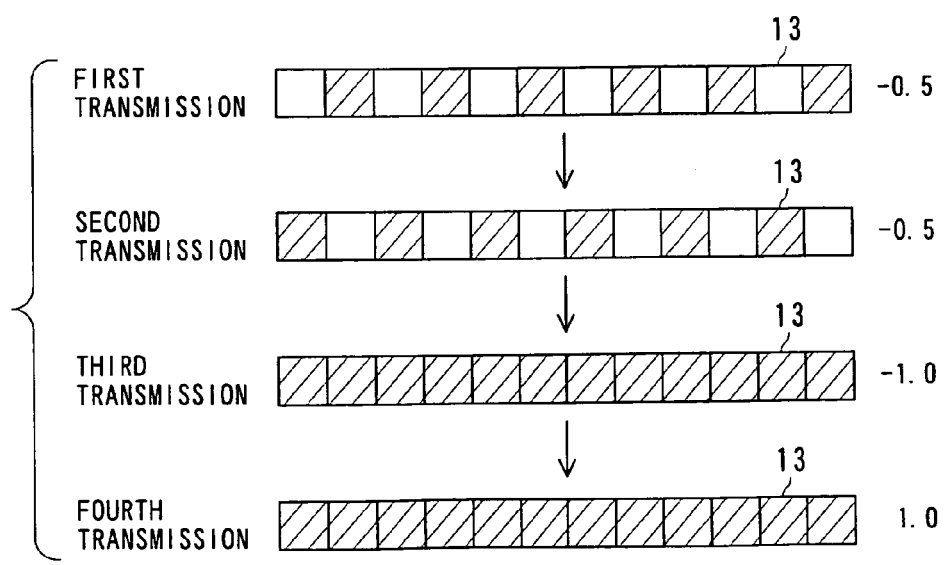
FIG. 6 is a diagram explaining a method for controlling the number of channels used in the ultrasonic probe to modulate the amplitude of transmission ultrasound in the ultrasonic diagnostic apparatus shown in FIG. 1.
Figure 7:
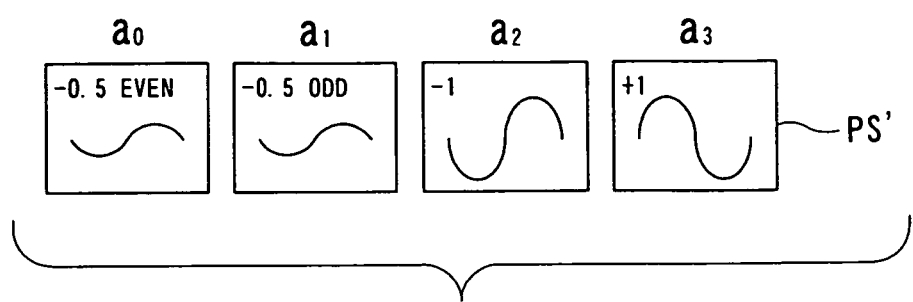
FIG. 7 is an example of a transmission pulse sequence when ultrasonic waves are transmitted by the method, shown in FIG. 6, for controlling the number of channels used in the ultrasonic probe.

FIG. 6 is a diagram explaining a method for controlling the number of channels used in the ultrasonic probe 13 to modulate the amplitude of transmission ultrasound in the ultrasonic diagnostic apparatus 10 shown in FIG. 1. FIG. 7 shows an example of a transmission pulse sequence PS' when ultrasonic waves are transmitted by the method, shown in FIG. 6, for controlling the number of channels used in the ultrasonic probe 13.

By the channel control in FIG. 6, transmission pulses can be generated such that the ratio in sound pressure is 0.5:1 at the same drive voltage according to the transmission pulse sequence PS' in FIG. 7. In the voltage control, in some cases, the linearity of the relationship between applied voltage and transmission ultrasound as an output is not held due to the nonlinearity of an electronic circuit. According to the control of the number of channels, control with high linearity can be achieved.

An arbitrary method for selecting channels to be driven in the ultrasonic probe 13 can be used. When the transducers are driven such that the even-numbered transducers and the odd-numbered transducers are driven independently of each other, an increase in grating lobe level can be suppressed.

In step S3, the ultrasonic probe 13 receives an echo signal from the object P and then supplies the signal to the receiver circuit 17. The preamp 17a amplifies the echo signal every channel. The A/D converter 17b converts the supplied signal into a digital signal. The rectified phase adding circuit 17c performs the phase-rectifying and adding process to the supplied echo signal to determine the directivity of ultrasound transmission and reception, thus producing an RF signal.

The RF signals generated by a plurality of ultrasound transmissions are temporarily stored in the line memory 17d.

In step S4, the operating interlines circuit 17e reads the RF signals from the line memory 17d and multiplies the RF signals by predetermined coefficients for receiving filter, thus producing a nonlinear signal. In other words, since ultrasound transmitted to the object P is subjected to AM or PM, a nonlinear signal based on AM and that based on PM are produced by gain compensation. The nonlinear signals are used for imaging.

Referring to FIG. 5, when the transmission pulse sequence is [−0.5, −1, 1], the RF signals are multiplied by respective weight coefficients of [2, −1, 0] as receiving filter coefficients. Thus, a nonlinear signal based on AM is obtained. When the RF signals are multiplies by receiving filter coefficients of [0, 1, 1], a nonlinear signal based on PM is obtained.

On condition that the transmission pulse sequence is [−0.5 (even), −0.5 (odd), −1 (all), 1 (all)] and the amplitude of transmission ultrasound is controlled by controlling the number of channels, when the RF signals are multiplied by receiving filter coefficients of [1, 1, −1, 0], the two RF signals at a sound pressure of 0.5 are combined at the aperture, so that a nonlinear signal based on AM is obtained. When the RF signals are multiplied by receiving filter coefficients of [0, 0, 1, 1], a nonlinear signal based on PM is obtained. The grating lobe in this case is the same as that in the use of all of the transducers.

Figure 8:
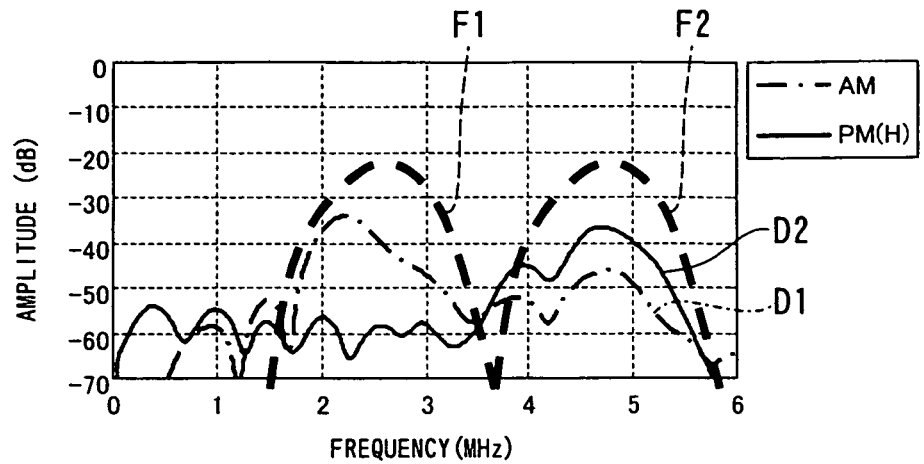
FIG. 8 is the spectrum of a nonlinear signal based on AM and that based on PM, the signals being obtained from tissue in the ultrasonic diagnostic apparatus shown in FIG. 1.
Figure 9:
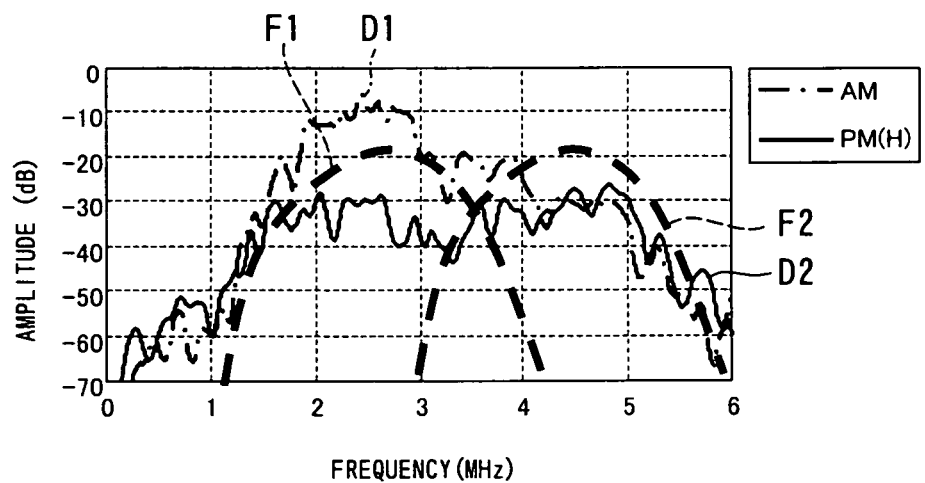
FIG. 9 is the spectrum of a nonlinear signal based on AM and that based on PM, the signals being obtained from an ultrasonic contrast medium in the ultrasonic diagnostic apparatus shown in FIG. 1.

FIG. 8 shows the spectrum of a nonlinear signal based on AM and that based on PM, the signals being obtained from tissue in the ultrasonic diagnostic apparatus 10 shown in FIG. 1. FIG. 9 shows the spectrum of a nonlinear signal based on AM and that based on PM, the signals being obtained from an ultrasonic contrast medium in the ultrasonic diagnostic apparatus 10 shown in FIG. 1.

In FIGS. 8 and 9, each dotted chain line D1 indicates the nonlinear signal based on AM and each solid line D2 indicates the nonlinear signals based on PM.

As shown in FIGS. 8 and 9, the nonlinear signals based on PM each include second higher harmonic components as main components. The nonlinear signals based on AM have peaks in both of the fundamental band and the second harmonic band.

The merits and demerits of imaging the nonlinear signal based on AM and imaging that based on PM will now be described. For imaging fundamental components of a nonlinear signal based on AM conventionally used, it is superior in penetration to imaging second higher harmonic components of the nonlinear signal based on AM. However, the former is inferior in resolution to the latter. Further, when PM is performed in addition to AM, imaging fundamental components of a nonlinear signal based on AM and PM is inferior in resolution to imaging second higher harmonic components thereof.

In other words, in imaging the fundamental components of the nonlinear signal, unfortunately, high resolution is incompatible with high penetration.

The reason why imaging the fundamental components of the nonlinear signal based on AM or both AM and PM is inferior in resolution to imaging the second higher harmonic components thereof is as follows: When the sound pressure of ultrasonic pulse varies, the resonant frequency of bubbles also changes, resulting in phase difference in received echoes obtained from transmission pulses with different sound pressures. In other words, in the nonlinear imaging including AM, signal components are generated in the fundamental band due to the phase difference. Since the original signal serves as fundamental wave, the resolution is comparable to fundamental wave. On the other hand, in imaging the second higher harmonic components, the center frequency of the second harmonic band is higher than the fundamental band, and further, the frequency band thereof is widened. Thus, the resolution can be increased.

For the penetration, in consideration of only frequency-dependent attenuation, when the second higher harmonic components is used, ultrasonic waves are transmitted at a lower frequency than the use of the fundamental components. This does not lead to the reason why the fundamental components of the nonlinear signal are preferably used. However, as one of the reasons why the fundamental components of the nonlinear signal are preferably used, the occurrence of THI components is less in the fundamental band.

In imaging the fundamental components of the nonlinear signal, even if the sound pressure of ultrasound is increased, the influence of THI components is less than imaging the second higher harmonic components thereof. In other words, when the fundamental components of the nonlinear signal are used for imaging, the sound pressure of ultrasound can be increased, thus increasing the penetration.

Another reason why the fundamental components of the nonlinear signal are preferably used is as follows: Pulses with different sound pressures are transmitted, resulting in phase difference. The phase difference can be detected from fundamental components. Thus, detection with high sensitivity can be realized.

From the above-mentioned viewpoints, when a target part of the object P is deep and higher penetration is required, it is preferable to use the fundamental components of the nonlinear signal in imaging. On the contrary, when the target part of the object P is shallow and higher resolution is required, it is preferable to use the second higher harmonic components of the nonlinear signal in imaging. The fundamental components of the nonlinear signal denote nonlinear signal components as reflected echoes in the transmission frequency band of ultrasound. The signal components may include a part of second higher harmonic components or third strain components.

Accordingly, both of the second higher harmonic components of the nonlinear signal based on PM and the fundamental components of the nonlinear signal based on AM are used for imaging. The nonlinear signal based on AM and that based on PM are supplied to the phase detecting circuit 17f. The components of each supplied signal are mixed at a predetermined frequency such that both of the second higher harmonic components of the nonlinear signal based on PM and the fundamental components of the nonlinear signal based on AM are extracted. After that, the resultant signals are filtered by the echo filter 17g.

As shown in FIGS. 8 and 9, for the nonlinear signals based on AM, both the fundamental components and the second higher harmonic components are extracted. The components of each nonlinear signal are mixed at about the center frequency f0 of transmission ultrasound into a base band signal. On the other hand, the nonlinear signals based on PM each include the second higher harmonic components as main. The components of each nonlinear signal are mixed at a frequency 2f0, that is twice as high as the center frequency f0 of transmission ultrasound, into a base band signal. The frequency for mixing varies depending on the depth of a target part in the object P.

The nonlinear signal produced based on AM is inferior in resolution to that based on PM but is superior in deep sensitivity thereto. On the other hand, the nonlinear signal obtained based on PM is superior in resolution to that based on AM but is inferior in deep sensitivity thereto.

The echo filter 17g filters the base band signal based on AM and that based on PM, produced by the phase detecting circuit 17f, using filter coefficients as shown by dashed lines F1 and F2 in FIGS. 8 and 9. The filter coefficients F1 and F2 are set so as to correspond to the base band signal based on AM and that based on PM, respectively. In filtering through the echo filter 17g, the filter coefficients F1 and F2 are subjected to fine adjustment according to the depth of a target part in the object P as usual.

When the effective range of the nonlinear signal corresponds to a wide band as shown in FIG. 9, the filter coefficients F1 and F2 are set so that a nonlinear signal in the wide band can be extracted.

The two base band signals based on AM and PM filtered using the filter coefficients F1 and F2 are supplied to each of the B-mode processing unit 19 and the color Doppler processing unit 21.

In step S5, the B-mode processing unit 19 obtains B-mode signal values $B_A$ and $B_P$ for each scan line from the two base band signals based on AM and PM. The B-mode signal values $B_A$ and $B_P$ constitute a B-mode image. In other words, as shown in FIG. 5, a detection circuit 19a detects the base band signal based on AM and that based on PM outputted from the receiver circuit 17 to obtain the B-mode signal values $B_A$ and $B_P$. A log compression circuit 19b compresses the signal values $B_A$ and $B_P$ according to logarithmic transformation. The resultant B-mode signal values $B_A$ and $B_P$ are supplied to the synthesizing interlines circuit 19c.

In step S6, the synthesizing interlines circuit 19c assigns weights to the B-mode signal value $B_A$ based on AM and the B-mode signal value $B_P$ based on PM according to the depth of a target part in the object P, respectively, such that when a target part in the object P is shallow, the weight for the B-mode signal value $B_P$ based on PM is larger, and when the target part in the object P is deep, the weight for the B-mode signal value $B_A$ based on AM is larger, and after that, adds the weighted values.

Consequently, as shown in FIG. 5, on the basis of the B-mode signal values $B_A$ and $B_P$, a B-mode signal B indicating the resolution and the penetration according to the depth of a target part in the object P is produced. In other words, irrespective of whether a target part in the object P is shallow or deep, the B-mode signal B with high sensitivity can be obtained. Further, the B-mode signal B can be obtained from a shallow target part in the object P at high resolution.

The B-mode signal B is supplied to the coordinate conversion memory 23 for the B-mode processing unit. In the memory 23, the value is converted into data of the orthogonal coordinate system based on spatial information. The data is supplied to the image processing unit 27. When a B-mode image alone is displayed, the converted B-mode signal B as data of the orthogonal coordinate system is supplied to a display monitor 33, so that the B-mode image is displayed.

On the other hand, an image obtained by mixing the B-mode image, a color Doppler image, a power Doppler image, and a velocity image or an image obtained by mixing the B-mode image and the power Doppler image can also be displayed. In this case, in steps S1 to S4 of FIG. 4, the nonlinear signal based on AM and that based on PM are produced in the same way as the case of obtaining the B-mode signal B.

Figure 10:
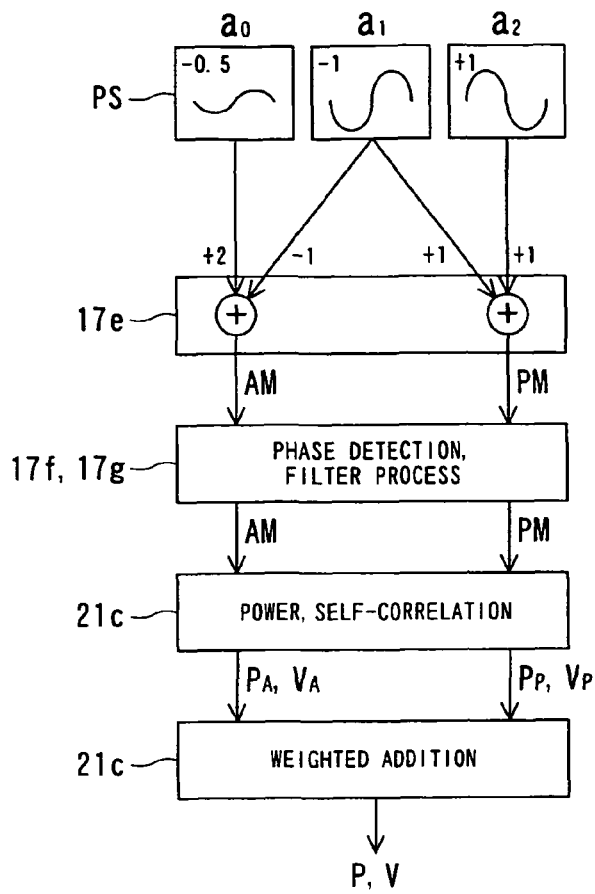
FIG. 10 is a procedure executed when the ultrasonic diagnostic apparatus of FIG. 1 simultaneously performs amplitude modulation and phase modulation, transmits amplitude-modulated and phase-modulated ultrasonic waves, and receives reflected waves to produce a power signal and a velocity signal through the color Doppler processing unit.

FIG. 10 shows a procedure executed when the ultrasonic diagnostic apparatus 10 of FIG. 1 simultaneously performs amplitude modulation and phase modulation, transmits amplitude-modulated and phase-modulated ultrasonic waves, and receives reflected waves to produce a power signal P and a velocity signal V through the color Doppler processing unit 21. As shown in FIG. 10, to produce the power signal P and the velocity signal V, in a manner similar to the case of obtaining the B-mode signal B in FIG. 5, a transmission pulse sequence is set to [−0.5, −1, 1] and the receiving filter coefficients are set to [2, −1, 0] and [0, 1, 1], thus obtaining a nonlinear signal based on AM and that based on PM.

The color Doppler processing unit 21 produces the power signal P and the velocity signal V from the obtained nonlinear signals. A power Doppler image and a velocity image are produced on the basis of the signals P and V.

In step S7, on the basis of the base band signal as the fundamental components based on AM and the base band signal as the harmonic components based on PM, power signal values $P_A$ and $P_P$ and velocity signal values $V_A$ and $V_P$ are obtained for each scan line. The power signal values $P_A$ and $P_P$ constitute a power image. The velocity signal values $V_A$ and $V_P$ constitute a velocity image.

In other words, the receiver circuit 17 outputs a time-series sequence of data composed of two base band signals in the fundamental and second harmonic bands based on AM and PM. The CTB 21a of the color Doppler processing unit 21 temporarily stores the data sequence. The stored data sequence of the base band signals is outputted to the wall filter 21b in a predetermined order. The wall filter 21b separates noise components from the base band signals as the fundamental and harmonic components and then supplies the resultant data to the velocity/dispersion/power estimation circuit 21c.

Instead of multiplying the RF signals by the receiving filter coefficients, the wall filter 21b can multiply the base band signals by the receiving filter coefficients.

As shown in FIG. 10, the velocity/dispersion/power estimation circuit 21c estimates the power signal values $P_A$ and $P_P$ composing a power image and the velocity signal values $V_A$ and $V_P$ composing a velocity image for each scan line on the basis of the base band signals as the fundamental and harmonic components based on AM and PM.

In step S8, the velocity/dispersion/power estimation circuit 21c assigns weights to the power signal values $P_A$ and $P_P$ and the velocity signal values $V_A$ and $V_P$ of the fundamental and harmonic components based on AM and PM according to the depth of a target part in the object P every time-series data sequence and then adds the paired weighted values, respectively. In other words, referring to FIG. 10, the two power signal values $P_A$ and $P_P$ of the fundamental and harmonic components based on AM and PM are weighted according to the depth of a target part in the object P such that when the target part in the object P is shallow, the weight for the power signal value $P_P$ based on PM is larger, and when the target part in the object P is deep, the weight for the power signal value $P_A$ based on $A_M$ is larger. The weighted values are then added into the power signal P.

The velocity signal values $V_A$ and $V_P$ are weighted in the same way as that for the power signal values $P_A$ and $P_P$. The weighted velocity signal values $V_A$ and $V_P$ are added into the velocity signal V.

The power signal P and the velocity signal V obtained by the weighted additions are subjected to logarithmic compression as necessary. After that, the resultant signals are supplied to the coordinate conversion memory 25 for the color Doppler processing unit. The coordinate conversion memory 25 converts each of the power signal P and the velocity signal V into data of the orthogonal coordinate system based on spatial information and then supplies the resultant data to the image processing unit 27.

The logarithmic compression for the velocity signal is not general. However, the logarithmic compression is of importance because aliasing velocity is high, alternatively, in order to distinguish between low-velocity blood-flow bubbles and tissue at low velocity.

The power signal P and the velocity signal V are supplied to the image processing unit 27, so that the B-mode image is synthesized with the velocity image or the power Doppler image.

First, in Step S9, which of the signals, B or P, V is used for a pixel value is determined according to the values of the signals B and P for the pixel on the image processing unit 27. This determination may be qualitatively performed according to the pre-designated function table.

Figure 11:
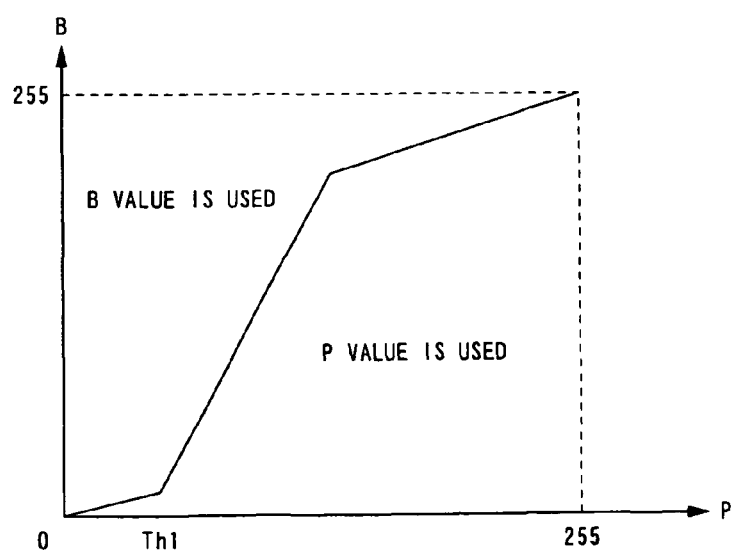
FIG. 11 is an example of a function table referred in determining whether the B-mode signal is used for a pixel value, or the power signal and the velocity signal are used in the ultrasonic diagnostic apparatus of FIG. 1.

FIG. 11 shows an example of a function table referred in determining whether the B-mode signal B is used for a pixel value, or the power signal P and the velocity signal V are used in the ultrasonic diagnostic apparatus 10 of FIG. 1.

In FIG. 11, the ordinate indicates the B-mode signal B and the abscissa denotes the power signal P.

As the function table shown in FIG. 11, when the signal P of the designated pixel is substantially small (power signal value P<first threshold Th1), the value of the signal B is used as the pixel value. The reason to indicate B-mode signal value B prior like this is because the signal P is noise in many cases when P<Th1. On the other hand, when P>TH1 or P=Th1, the value P of power signal and the value V of velocity signal corresponding to P is indicated prior because the power signal value P represents blood flow information.

More, the threshold for the function table may not necessarily be a fixed value as long as the B-mode signal value B and the power signal value P are to be compared to select one of them. For example, the function table in FIG. 11 is determined by three linear functions.

Thus the signal value information for each pixel is determined and output to the multiplexer 27b. The multiplexer 27b selectively outputs the B-mode signal value B, the power signal value P, or the velocity signal value V for each pixel according to the input information to the color map memory 27c.

Then in the step S10, a color is assigned to each pixel in the color map memory 27c. Assigning of colors for each pixel is performed as in the following example. If the B-mode signal value B is used for the pixel, the color assignment is performed as Red=Green=Blue=B value (0-255), which means the pixel is displayed in gray scale.

Figure 12:
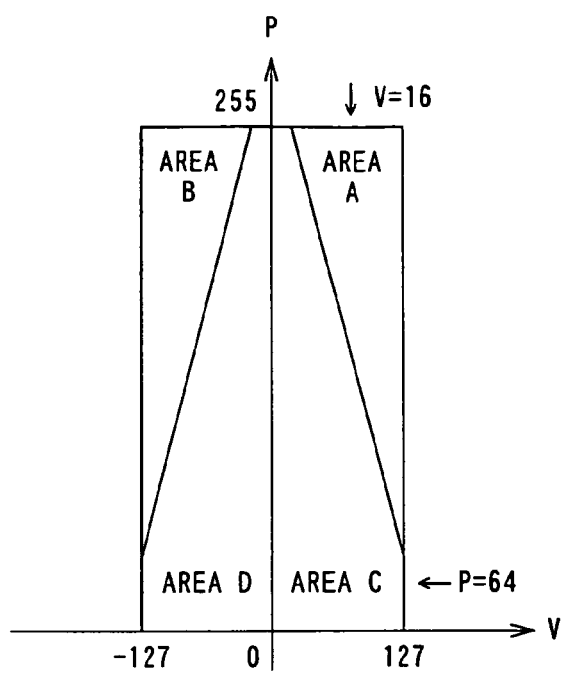
FIG. 12 is an example of a color map used in image processing of the ultrasonic diagnostic apparatus indicated in FIG. 1.

FIG. 12 shows an example of a color map used in image processing of the ultrasonic diagnostic apparatus 10 indicated in FIG. 1.

On the other hand, if the power signal value P and the velocity signal value V are used for the pixel, its color changed on the sizes of the power signal value P and the velocity signal value V for the pixel is assigned according to a color map divided into four areas based on the power signal value P and the velocity signal value V as shown in FIG. 12. The following is an example of the coloring rule assuming the power signal value P=0-255, the velocity signal value V=(−128)-(+127) indicated by using a formula (1-1), a formula (1-2), a formula (1-3) and a formula (1-4).

Area A. Red is assigned. (when P>320−2×|V| and V≧0)

$$Red=min(1.12 \times P, 255)$$

$$Green=Blue=0.98 \times P \qquad (1\text{-}1)$$

Area B. Blue is assigned. (when P>320−2×|V| and V<0)

$$Blue=min(1.12 \times P, 255)$$

$$Red=Blue=0.98 \times P \qquad (1\text{-}2)$$

Area C. Red-Green is assigned. (when P<320−2×|V| and V≧0)

$$R1=\min(1.12\times P, 255)$$

$$G1=B1=0.98\times P$$

$$R2=B2=0.9\times P$$

$$G2=\min(P\times 1.25, 255)$$

$$a=|V|/(160-P/2)$$

$$\text{Red}=a\times R1+(1-a)\times R2$$

$$\text{Green}=a\times G1+(1-a)\times G2$$

$$\text{Blue}=a\times B1+(1-a)\times B2 \quad (1\text{-}3)$$

Area D. Blue-Green is assigned. (when P<320−2×|V| and V<0)

$$B1=\min(1.12\times P, 255)$$

$$R1=G1=0.98\times P$$

$$R2=B2=0.9\times P$$

$$G2=\min(P\times 1.25, 255)$$

$$a=|V|/(160-P/2)$$

$$\text{Red}=a\times R1+(1-a)\times R2$$

$$\text{Green}=a\times G1+(1-a)\times G2$$

$$\text{Blue}=a\times B1+(1-a)\times B2 \quad (1\text{-}4)$$

Figure 13:
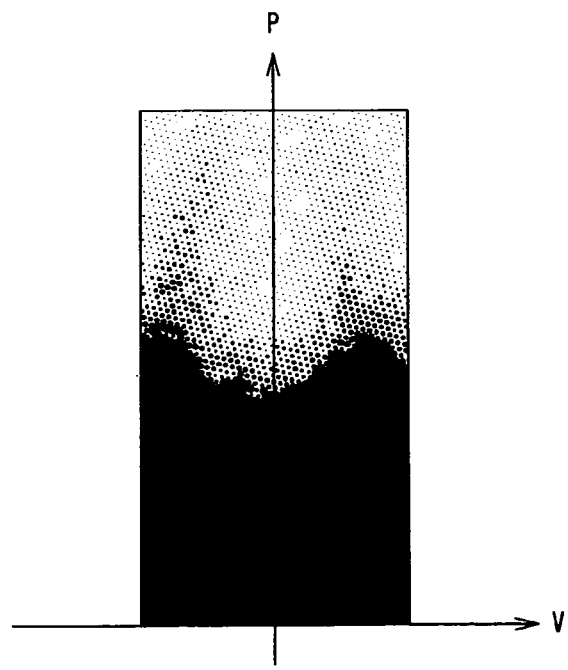
FIG. 13 is an example of a color map used in image processing of the ultrasonic diagnostic apparatus indicated in FIG. 1.

FIG. 13 shows an example of a color map used in image processing of the ultrasonic diagnostic apparatus 10 indicated in FIG. 1.

Based on these processes of color assignment, living body information of the object P is displayed according to the following color and brightness assignment as shown in a color map in FIG. 13. (1) Bubbles flowing in a fast blood flow such in an artery: red or blue according to the direction; (2) Bubbles in a slow blood flow in a vein: green; (3) Bubbles in tissues: dark green because of the small velocity and power; and (4) Non-contrast tissues: gray scale.

These four colors (red, blue, green and gray) gradually change at the boundaries and the operator observing the timing of contrast enhancement or continuity of blood cells can manually determine the color map in the end.

A remaining clatter in the fundamental component would have a fast velocity close to the Nyquist velocity. And its power is small due to the suppression by the LPF. When the velocity is close to the Nyquist and the power is small, the pixel is displayed with a gradation close to the grayscale. This makes it possible for the operator to observe an image as a B-mode tissue image while it actually is a power image.

Next, the image synthesized with signals B, P, and V in the image processing circuit 27 is displayed in the monitor 33 (Step S11). Thus, the operator may observe the synthesized image.

The series of the procedures of steps S1-S11 discussed above are normally repeated in real time during an examination. This makes it possible for the operator to observe ultrasonic image at real time on the monitor 33 like the following sample form.

Figure 14:
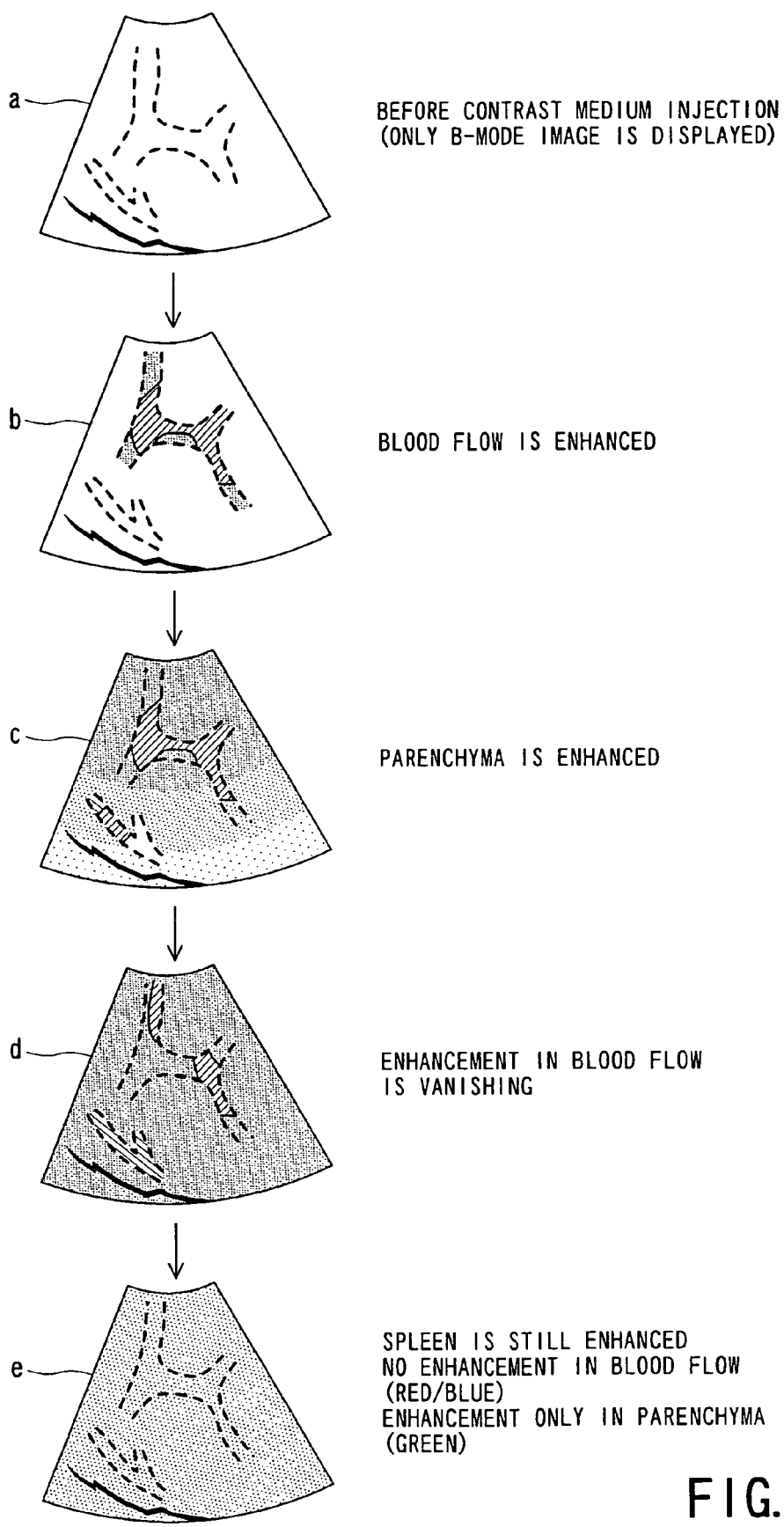
FIG. 14 is a diagram explaining a synthesized image (of, e.g., liver) which an observer can observe at a display monitor.

FIG. 14 is a diagram explaining a synthesized image (of, e.g., liver) which an observer can observe at a display monitor 33.

First, as shown in the image a, since the signal intensity P is very small and there is no contrast enhancement before the contrast medium is injected, the value B is used for every pixel value to display a B-mode-only image.

Then 5-10 seconds after the injection, the image shows large blood vessels enhanced with red or blue coloring as shown in the image b. In this figure, hatched areas represent contrast-enhanced blood flows. According to the above-mentioned color assignment throughout the image a to e, right-slanted hatching corresponds to red and left-slanted hatching corresponds to blue.

The image c shows the ultrasonic image 10-30 seconds after the injection in which the medium enters into the capillary vessels and the whole tissues (parenchyma) are enhanced. The dotted areas represent the enhanced parenchyma. These areas are colored in green. The areas where the medium does not enter (such as a diaphragm) are displayed as a B-mode image.

Approximately 30-300 seconds after the injection, the contrast enhancement in the blood flow gradually diminishes in the displayed image as shown in the image d.

More than 5 minutes after the injection, as shown in the image e, the displayed image shows enhanced parenchyma, such as a spleen or liver, in which the contrast medium tends to remain.

The ultrasonic diagnostic apparatus 10 discussed above males it possible to get the following some additional advantages.

The ultrasonic diagnostic apparatus 10 with high penetration and high spatial resolution can be provided. In other words, in the ultrasonic diagnostic apparatus 10, transmission ultrasound is subjected to amplitude modulation (AM) and phase modulation (PM) to obtain a nonlinear signal of fundamental wave area based on AM and a nonlinear signal of second higher harmonic wave based on PM. The B-mode signal values $B_A$ and $B_P$, the power signal values $P_A$ and $P_P$, and the velocity signal values $V_A$ and $V_P$ obtained from the nonlinear signals are weighted according to the depth of a target part in the object P and the paired weighted values are then added, respectively, thus obtaining the B-mode signal B, the power signal P, and the velocity signal V.

Therefore, when a target part in the object P is deep and higher penetration is required, the fundamental components of the nonlinear signal effective in improving the penetration are used for imaging. On the other hand, when a target part in the object P is shallow and higher resolution is required, the nonlinear signal of the second higher harmonic components effective in increasing the resolution are used for imaging. Thus, an image can be formed at high sensitivity irrespective of the depth of the target part in the object P. In addition, an image can be formed at high resolution in a shallow part in the object P.

The ultrasonic diagnostic apparatus 10 of this embodiment produces an ultrasonic image according to the power and blood velocity signals selectively in a portion where blood flow information is available with the Contrast Echo method. Therefore, the ultrasonic diagnostic apparatus 10 can indicate a blood flow image which indicates correct blood flow directions. Furthermore, in the parenchyma (tissue), it is possible to display an ultrasonic image in which blood flow, contrast-enhanced parenchyma and non-contrast tissues can be clearly distinguished since different colors are assigned according to the signal intensity. In other words, for instance, before contrast medium injection, only B-mode information is displayed in grayscale. When blood flow in the blood vessel is contrast-enhanced, the direction of blood flow is displayed in red or blue. When blood flow in parenchyma is contrast-enhanced, an image displayed in green can be obtained at high penetration and high resolution.

Furthermore, the ultrasonic diagnostic apparatus 10 is capable of imaging changes in time of bubbles as a synthesized image of B-mode, power and velocity signals with the Contrast Echo method. Furthermore, it is possible to display an ultrasonic image in which blood flow, contrast-enhanced parenchyma and non-contrast tissues can be clearly distinguished.

Further, the ultrasonic diagnostic apparatus 10 can correctly estimate flow velocity using nonlinear signals. In other words, the ultrasonic diagnostic apparatus 10 transmits two kinds of ultrasonic pulses such that the MI of one pulse is 0.05 and that of the other one is 0.1 using a contrast medium which realizes enhancement at low MI, e.g., Sono Vue, the Bracco's ultrasonic contrast medium, and then receives reflected waves. As mentioned above, both the amplitudes and the phases of the pulses are modulated to extract fundamental components and second higher harmonic components of nonlinear signals. The nonlinear signals are weighted according to the depth of a target part in the object P and are then added. Velocity estimation is performed using the result of the weighted addition.

In experiments of the present inventor, velocity estimation based on the nonlinear signals extracted by the ultrasonic diagnostic apparatus 10 was substantially close to that based on linear signals obtained when the MI was 1.0 with no contrast medium. Thus, a blood-flow image correctly indicating the direction of blood flow can be displayed by contrast echo imaging.

For example, in the use of Levovist, the Schering's ultrasonic contrast medium, unless bubbles are disrupted at high MI, enhancement is not achieved. Therefore, flow velocity cannot be obtained correctly by a similar or different technique.

Modifications of the transmission pulse sequence and modifications of the receiving filter coefficients will now be described. The transmission pulse sequence and the receiving filter coefficients can be varied in addition to the above-mentioned values.

For example, when a transmission pulse sequence is set to [0.5, −0.5, 1], receiving filter coefficients for AM are set to [0, 2, −1], and receiving filter coefficients for PM are set to [2, 2, 0], transmission sound pressure for PM can be reduced to 0.5. In PM, second higher harmonic components of a nonlinear signal are used for imaging. As the sound pressure is larger, the amount of THI components reflected from tissue becomes larger. Unfortunately, in contrast echo imaging using an ultrasonic contrast medium, the THI components cause a problem. Therefore, it is useful to reduce the transmission sound pressure for PM. On the other hand, for AM, fundamental components of a nonlinear signal are used for imaging. Accordingly, the occurrence of the THI components is less. Even when the sound pressure is large to some extent, only signals reflected from the contrast medium can be extracted.

For example, the number of channels is controlled to control the amplitude of transmission ultrasound, ultrasound is transmitted five times according to a transmission pulse sequence of [−0.5 (even), −0.5 (odd), 0.5 (even), 0.5 (odd), −1 (all)], receiving filter coefficients for AM are set to [0, 0, 1, 1, −1], and receiving filter coefficients for PM are set to [1, 1, 1, 1, 0]. The advantage equivalent to that in the case where the transmission pulse sequence of [0.5, −0.5, 1] is used, the receiving filter coefficients for AM are set to [0, 2, −1], and the receiving filter coefficients for PM are set to [2, 2, 0], where the transmission sound pressure for PM is reduced, can be obtained.

Further, ultrasound can be transmitted four times according to a transmission pulse sequence of [−0.5, 1, −1, 0.5] and six patterns of receiving filter coefficients, e.g., [−2, 0, 1, 0], [2, 0, 0, 2], [0, 1, 1, 0], [0, 0, 1, 2], [2, 1, 0, 0], and [1, 0.5, −0.5, −1] can be set.

In this case, when the receiving filter coefficients are set to [−2, 0, 1, 0], a nonlinear signal based on AM can be obtained. When the receiving filter coefficients are set to [2, 0, 0, 2] or [0, 1, 1, 0], a nonlinear signal based on PM can be obtained. In the use of the former pattern, the nonlinear signal based on PM(L) is obtained. The PM(L) means that the transmission sound pressure is reduced. In the use of the latter pattern, the nonlinear signal based on PM(H) is obtained. The PM(H) means that the transmission sound pressure is not reduced.

When the receiving filter coefficients are set to [0, 0, 1, 2], [2, 1, 0, 0], or [1, 0.5, −0.5, −1], a nonlinear signal based on both AM and PM can be obtained.

The RF signals are multiplied by the six patterns of receiving filter coefficients to produce nonlinear signals. The components of the nonlinear signals are mixed at the same or different center frequencies, thus detecting the phases. In the synthesizing interlines circuit 19c, according to the depth of a target part in the object P, the signals of the six patterns are subjected to weighted addition using multiplying different echo filter coefficients.

In other words, the transmission pulse sequence and the various receiving filter coefficients are set to produce the nonlinear signal based on AM, that based on PM(L), that based on PM(H), and that based on both AM and PM. The required frequency band components of the nonlinear signals can be extracted and be used for imaging. The nonlinear signals produced by various modulations are used in combination for imaging, so that the influences by transmission sound pressure and modulations are controlled according to the depth of a target part in the object P. Thus, the ultrasonic diagnostic apparatus 10 with high resolution and high penetration can be provided.

Figure 15:
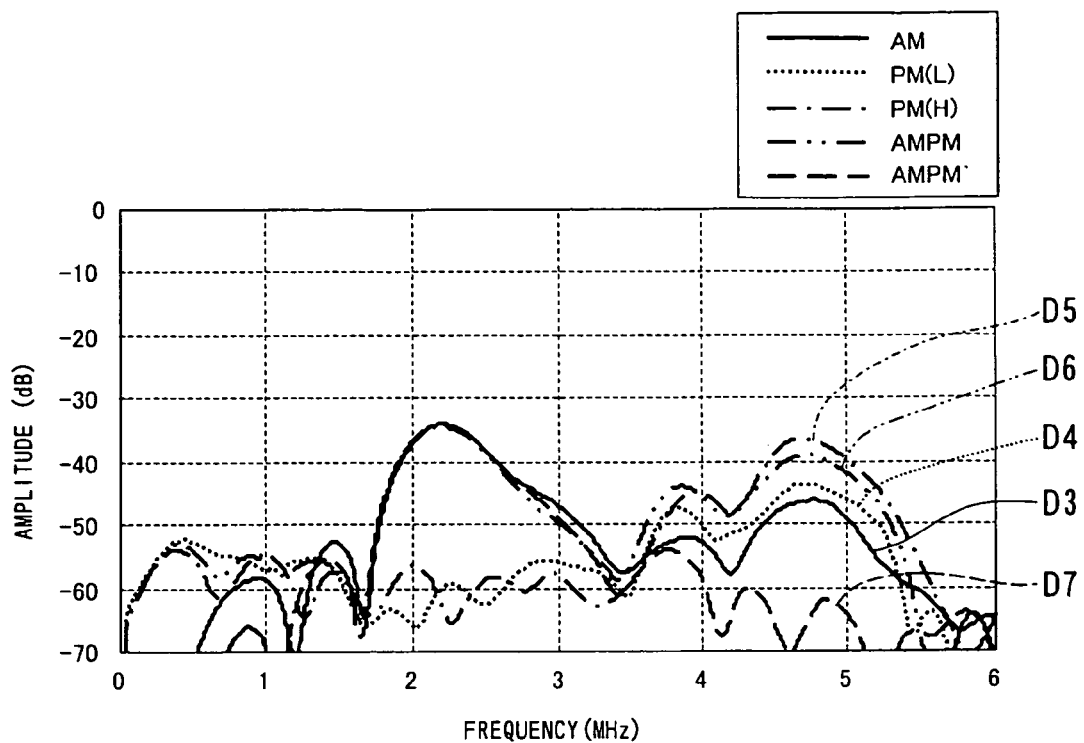
FIG. 15 is the spectra of nonlinear signals, reflected from tissue, obtained by various modulations in the ultrasonic diagnostic apparatus shown in FIG. 1.
Figure 16:
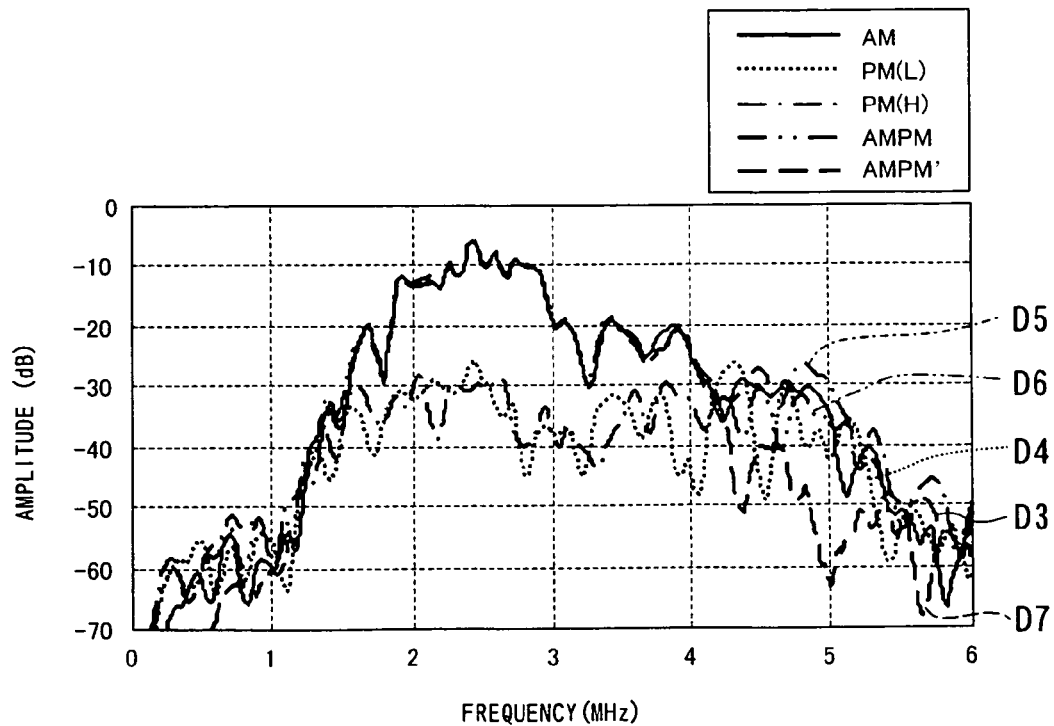
FIG. 16 is the spectra of nonlinear signals, reflected from an ultrasonic contrast medium, obtained by various modulations in the ultrasonic diagnostic apparatus shown in FIG. 1.

FIG. 15 shows the spectra of nonlinear signals, reflected from tissue, obtained by various modulations in the ultrasonic diagnostic apparatus 10 shown in FIG. 1. FIG. 16 shows the spectra of nonlinear signals, reflected from an ultrasonic contrast medium, obtained by various modulations in the ultrasonic diagnostic apparatus 10 shown in FIG. 1.

In FIGS. 15 and 16, each solid line D3 indicates the nonlinear signal obtained by amplitude modulation (AM). Each dotted line D4 indicates the nonlinear signal obtained by phase modulation [PM(L)] in which the transmission sound pressure is reduced. Each dotted-chain line D5 indicates the nonlinear signal produced by phase modulation [PM(H)] in which the transmission sound pressure is not reduced. Each double-dotted chain line D6 indicates the nonlinear signal obtained by both amplitude modulation and phase modulation (AMPM). Each dashed line D7 indicates the nonlinear signal obtained by both another amplitude modulation and another phase modulation (AMPM').

As shown in FIGS. 15 and 16, the nonlinear signals obtained by PM(L) and PM(H) each include second higher harmonic components as main. The nonlinear signals obtained by AM and AMPM each have peaks in the fundamental and second harmonic bands. The nonlinear signals obtained by AMPM' each include fundamental components as main.

The nonlinear signal obtained by AM, that obtained by AMPM, and that obtained by AMPM' are converted into base band signals by mixing the components thereof at different center frequencies near the center frequency f0 of transmission ultrasound. The respective base band signals are multiplied by echo filter coefficients. On the other hand, the nonlinear signal obtained by PM(L) and that obtained by PM(H) are converted into base band signals by mixing the components thereof at different frequencies near a frequency 2f0, that is approximately twice as high as the center frequency f0 of transmission ultrasound. The respective base band signals are multiplied by echo filter coefficients. Each frequency for mixing is changed depending on the depth of a target part in the object P.

As shown in FIG. 16, when the effective range of the nonlinear signal corresponds to a wide band, the filter coefficients are set so that the nonlinear signal in the wide band can be extracted.

Modifications of the transmission pulse sequence and the receiving filter coefficients to produce an only nonlinear signal based on both amplitude modulation and phase modulation (AMPM) of transmission ultrasound will now be described.

For example, a transmission pulse sequence can be set to [0.5, −1] and receiving filter coefficients can be set to [2, 1]. Both the phase and the amplitude of transmission ultrasound are changed using the transmission pulse sequence and the receiving filter coefficients to produce a nonlinear signal.

Figure 17:
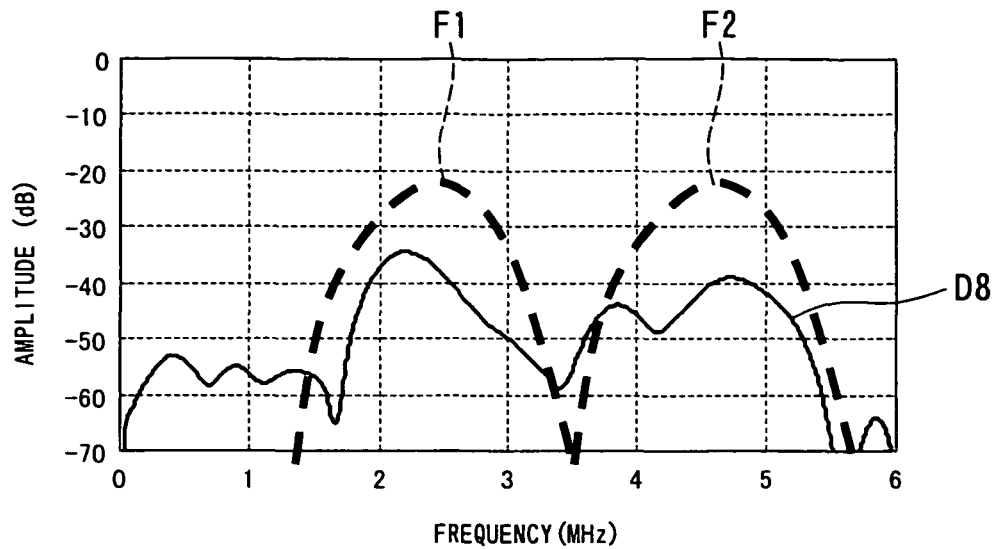
FIG. 17 is the spectrum of a nonlinear signal from tissue, the signal being obtained by both amplitude modulation and phase modulation (AMPM) through the ultrasonic diagnostic apparatus shown in FIG. 1.
Figure 18:
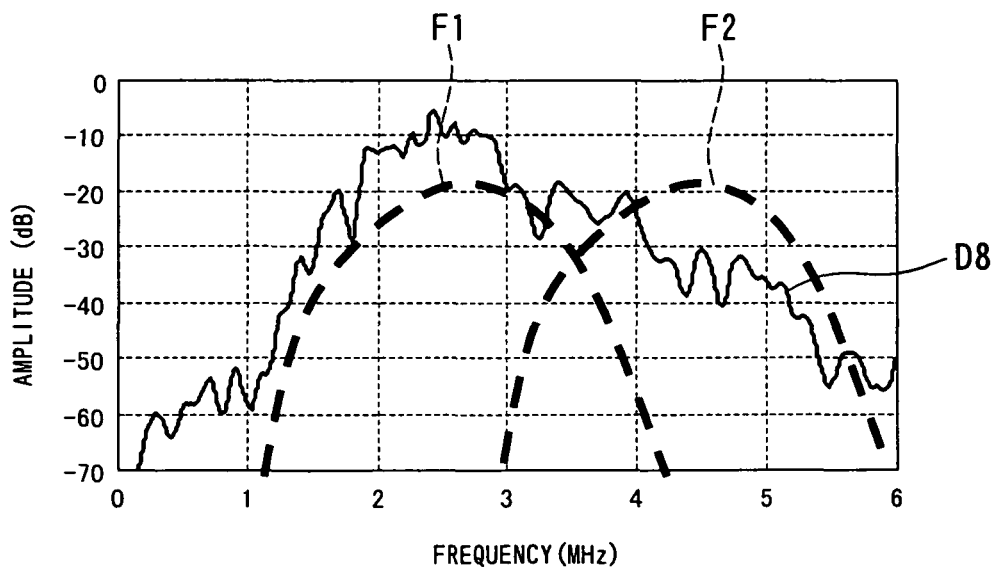
FIG. 18 is the spectrum of a nonlinear signal from an ultrasonic contrast medium, the signal being obtained by both amplitude modulation and phase modulation (AMPM) through the ultrasonic diagnostic apparatus shown in FIG. 1.

FIG. 17 shows the spectrum of a nonlinear signal from tissue, the signal being obtained by both amplitude modulation and phase modulation (AMPM) through the ultrasonic diagnostic apparatus 10 shown in FIG. 1. FIG. 18 shows the spectrum of a nonlinear signal from an ultrasonic contrast medium, the signal being obtained by both amplitude modulation and phase modulation (AMPM) through the ultrasonic diagnostic apparatus 10 shown in FIG. 1.

In FIGS. 17 and 18, each solid line D8 indicates the nonlinear signal obtained by AMPM.

As shown in FIG. 17, the spectrum of the nonlinear signal from tissue obtained by AMPM has peaks in the fundamental band and the second harmonic band. Accordingly, the nonlinear signal components centered at a plurality of frequencies can be extracted using, e.g., two filters F1 and F2 (F1<F2). Further, B-mode signal values $B_A$ and $B_P$, power signal values $P_A$ and $P_P$, velocity signal values $V_A$ and $V_P$ obtained from the extracted nonlinear signal components in the fundamental and second harmonic bands are weighted. The paired weighted values are added, respectively.

The weighting coefficients for weighted addition are set according to the depth of a target part in the object P in such a manner that the weighting coefficient for the B-mode signal value $B_P$, the power signal value $P_P$, and the velocity signal value $V_P$ filtered by the high-frequency filter F2 are larger than that for the values $B_A$, $P_A$, and $V_A$ with respect to a shallow part of the object P in order to assure high resolution, and with respect to a deep part of the object P, the weighting coefficient for the B-mode signal value $B_A$, the power signal value $P_A$, and the velocity signal value $V_A$ filtered by the low-frequency filter F1 is larger in order to assure high penetration.

On the other hand, referring to FIG. 18, the spectrum of the nonlinear signal from the ultrasonic contrast medium obtained by AMPM has a wide peak in the fundamental and second harmonic bands. In the same way as the case of the nonlinear signal from tissue, the nonlinear signal components centered at a plurality of frequencies can be extracted using, e.g., two filters F1 and F2 (F1<F2). The extracted nonlinear signal components are subjected to weighted addition by the same technique as that for the nonlinear signal from tissue and are then used for imaging.

In other words, when not only frequency compounding, i.e., filtering the nonlinear signal through the different filters F1 and F2 and compounding, is performed but also scanning with special modulations AMPM is performed, the spectrum of the nonlinear signal from tissue has two peaks and that of the nonlinear signal from the contrast medium has a relatively wide band. The frequency compounding is performed using the above characteristics.

Instead of the use of the transmission pulse sequence of [0.5, −1] and the receiving filter coefficients of [2, 1], ultrasound is transmitted three times according to a transmission pulse sequence of [0.5 (even), 0.5 (odd), −1 (all)] and receiving filter coefficients of [1, 1, 1] for AMPM are used such that the amplitude of ultrasound transmitted by controlling the number of using channels can be modulated, thus eliminating an influence by the nonlinearity of an electric circuit.

In the above-mentioned ultrasonic diagnostic apparatus 10, the log-compressed B-mode signal values $B_A$ and $B_P$, power signal value $P_A$ and $P_P$, and velocity signal values $V_A$ and $V_P$ are subjected to weighted addition. Other values, which are being processed into the above values, can be subjected to weighted addition.

The values to be subjected to weighted addition include echo-filter output signals filtered with receiving filter from the echo filter 17g, detection output signals detected phases from the B-mode processing unit 19 or the color Doppler processing unit 21, log-compressed output signals, and coordinate-converted output signals from the coordinate conversion memory 23 or 25.

The weighted addition to the echo-filter output signals filtered with receiving filter is coherent addition. Since the center frequencies of nonlinear signals are close to DC, so long as the signals are in phase, there is no adverse effect by the addition.

On the other hand, the weighted addition to the detection output signals detected phases from the B-mode processing unit 19 or the color Doppler processing unit 21, the log-compressed output signals, and the coordinate-converted output signals from the coordinate conversion memory 23 or 25 is incoherent addition. This presents no problem with respect to phase.

When only B-mode images are formed using nonlinear signals, the components for producing nonlinear signals, i.e., the operating interlines circuit 17e and the phase detecting circuit 17f can be provided for the B-mode processing unit 19, instead of the receiver circuit 17.

What is claimed is:

1. An ultrasonic diagnostic apparatus comprising:
an ultrasonic transmitter unit configured to transmit an ultrasonic wave varied in at least one of phase and amplitude to an object;
an ultrasonic receiving unit configured to receive ultrasonic echoes generated by transmitting the ultrasonic wave;
an extracting unit configured to extract a first nonlinear signal obtained through modulating the amplitude of the ultrasonic wave and a second nonlinear signal obtained through modulating the phase of the ultrasonic wave from common ultrasonic echoes on a same scanning line;
a filter unit configured to execute either a filter process or a process equivalent to the filter process either to the first nonlinear signal and the second nonlinear signal or to the first nonlinear signal processed by a designated process and the second nonlinear signal processed by the designated process with at least two different sets of a middle frequency and a width of a band to extract a second higher harmonic component and a fundamental component; and an adder unit configured to perform weighted addition to the first nonlinear signal and the second nonlinear signal for imaging by
(a) changing a first weight value and a second weight value depending on a depth of the object,
(b) multiplying the first nonlinear signal by the first weight value to generate a first weighted nonlinear signal,
(c) multiplying the second nonlinear signal by the second weight value to generate a second weighted nonlinear signal, and
(d) then adding together the first weighted nonlinear signal and the second weighted nonlinear signal;
wherein the adder unit further configured to perform the weighted addition by assigning a larger weight coefficient for multiplying the second nonlinear signal than a weight coefficient for multiplying the first nonlinear signal when a target part in the object is relatively shallow, and by assigning a larger weight coefficient for multiplying the first nonlinear signal than a weight coefficient for multiplying the second nonlinear signal when the target part in the object is relatively deep.

2. An ultrasonic diagnostic apparatus according to claim 1, wherein the adder unit further configured to perform weighted addition to B-mode signal values obtained through the first nonlinear signal and the second nonlinear signal subjected to either the filter process or the process equivalent to the filter process and to at least one of velocity signal values and power signal values obtained through the first nonlinear signal and the second nonlinear signal subjected to either the filter process or the process equivalent to the filter process, and
further comprising an image processing unit configured to synthesize at least one of a power image obtained through the power signal values performed weighted addition and a velocity image obtained through the velocity signal values performed weighted addition to a B-mode image obtained through the B-mode signal values performed weighted addition.

3. An ultrasonic diagnostic apparatus according to claim 1, wherein the ultrasonic receiving unit is configured to receive the ultrasonic echoes from the object injected a contrast medium.

4. An ultrasonic diagnostic apparatus comprising:
an ultrasonic transmitter unit configured to transmit an ultrasonic wave varied in phase and amplitude to an object;
an ultrasonic receiving unit configured to receive ultrasonic echoes generated by transmitting the ultrasonic wave;
an extracting unit configured to extract first and second nonlinear signals obtained from the ultrasonic echoes by modulating the phase and the amplitude of the ultrasonic wave;
a filter unit configured to execute either a filter process or a process equivalent to the filter process either to the nonlinear signal or to the nonlinear signal processed by a designated process with at least two different sets of a middle frequency and a width of a band to extract a second higher harmonic component and a fundamental component; and
an adder unit configured to perform weighted addition to the first and second nonlinear signals for imaging by
(a) changing a first weight value and a second weight value depending on a depth of the object,
(b) multiplying the first nonlinear signal by the first weight value to generate a first weighted nonlinear signal,
(c) multiplying the second nonlinear signal by the second weight value to generate a second weighted nonlinear signal, and
(d) then adding together the first weighted nonlinear signal and the second weighted nonlinear signal;
wherein the adder unit further configured to perform the weighted addition by assigning a larger weight coefficient for multiplying the second nonlinear signal than a weight coefficient for multiplying the first nonlinear signal when a target part in the object is relatively shallow, and by assigning a larger weight coefficient for multiplying the first nonlinear signal than a weight coefficient for multiplying the second nonlinear signal when the target part in the object is relatively deep.

5. An ultrasonic diagnostic method comprising:
transmitting an ultrasonic wave varied in at least one of phase and amplitude to an object;
receiving ultrasonic echoes generated by transmitting the ultrasonic wave;
extracting a first nonlinear signal obtained through modulating the amplitude of the ultrasonic wave and a second nonlinear signal obtained through modulating the phase of the ultrasonic wave from common ultrasonic echoes on a same scanning line;
executing either a filter process or a process equivalent to the filter process either to the first nonlinear signal and the second nonlinear signal or to the first nonlinear signal processed by a designated process and the second nonlinear signal processed by the designated process with at least two different sets of a middle frequency and a width of a band to extract a second higher harmonic component and a fundamental component; and
performing weighted addition to the first nonlinear signal and the second nonlinear signal for imaging by
(a) changing a first weight value and a second weight value depending on a depth of the object,
(b) multiplying the first nonlinear signal by the first weight value to generate a first weighted nonlinear signal,
(c) multiplying the second nonlinear signal by the second weight value to generate a second weighted nonlinear signal, and
(d) then adding together the first weighted nonlinear signal and the second weighted nonlinear signal;
wherein the performing weighted addition performs the weighted addition by assigning a larger weight coefficient for multiplying the second nonlinear signal than a weight coefficient for multiplying the first nonlinear signal when a target part in the object is relatively shallow, and by assigning a larger weight coefficient for multiplying the first nonlinear signal than a weight coefficient for multiplying the second nonlinear signal when the target part in the object is relatively deep.

6. An ultrasonic diagnostic method comprising:
transmitting an ultrasonic wave varied in phase and amplitude to an object receiving ultrasonic echoes generated by transmitting the ultrasonic wave;
extracting first and second nonlinear signals obtained from the ultrasonic echoes by modulating the phase and the amplitude of the ultrasonic wave;
executing either a filter process or a process equivalent to the filter process either to the nonlinear signal and to the nonlinear signal processed by a designated process with at least two different sets of a middle frequency and a width of a band to extract a second higher harmonic component and a fundamental component; and
performing weighted addition to the first and second nonlinear signals for imaging by (a) changing a first weight value and a second weight value depending on a depth of the object,
(b) multiplying the first nonlinear signal by the first weight value to generate a first weighted nonlinear signal,
(c) multiplying the second nonlinear signal by the second weight value to generate a second weighted nonlinear signal, and
(d) then adding together the first weighted nonlinear signal and the second weighted nonlinear signal;

wherein the performing weighted addition performs the weighted addition by assigning a larger weight coefficient for multiplying the second nonlinear signal than a weight coefficient for multiplying the first nonlinear signal when a target part in the object is relatively shallow, and by assigning a larger weight coefficient for multiplying the first nonlinear signal than a weight coefficient for multiplying the second nonlinear signal when the target part in the object is relatively deep.

* * * * *